United States Patent
De Benedetto et al.

(10) Patent No.: US 12,290,358 B2
(45) Date of Patent: May 6, 2025

(54) PULSE OXIMETRY METHODS, DEVICES AND SYSTEMS

(71) Applicant: LIFE METER SRL, Chieti (IT)

(72) Inventors: Fernando De Benedetto, Chieti (IT); Matteo Aventaggiato, Chieti (IT); Marco Raimondi, Chieti (IT); Alberto Visconti, Chieti (IT)

(73) Assignee: LIFE METER SRL, Chieti (IT)

( * ) Notice: Subject to any disclaimer, the term of this patent is extended or adjusted under 35 U.S.C. 154(b) by 0 days.

(21) Appl. No.: 17/767,802

(22) PCT Filed: Oct. 9, 2020

(86) PCT No.: PCT/EP2020/078516
§ 371 (c)(1),
(2) Date: Apr. 8, 2022

(87) PCT Pub. No.: WO2021/069729
PCT Pub. Date: Apr. 15, 2021

(65) Prior Publication Data
US 2024/0081696 A1   Mar. 14, 2024

(30) Foreign Application Priority Data
Oct. 9, 2019   (GB) .................................... 1914632

(51) Int. Cl.
*A61B 5/1455*   (2006.01)
*A61B 5/00*   (2006.01)
(Continued)

(52) U.S. Cl.
CPC ........ *A61B 5/14551* (2013.01); *A61B 5/0205* (2013.01); *A61B 5/1495* (2013.01);
(Continued)

(58) Field of Classification Search
CPC . A61B 5/1455; A61B 5/14551; A61B 5/6824; A61B 5/72; A61B 5/02416; A61B 5/681; A61B 2560/0233
See application file for complete search history.

(56) References Cited

U.S. PATENT DOCUMENTS 7,254,425 B2 *   8/2007   Lowery ................ A61B 5/1455
                                              600/310
10,194,808 B1   2/2019   Thompson et al.
(Continued)

FOREIGN PATENT DOCUMENTS

GB   2572626   10/2019
WO   2016178986   11/2016
(Continued)

OTHER PUBLICATIONS

Rusch et al. "Signal Processing Methods for Pulse Oximetry", Computers in Biology and Medicine, New York, NY, vol. 26, No. 2, published Mar. 1, 1996.
(Continued)

*Primary Examiner* — Eric F Winakur
(74) *Attorney, Agent, or Firm* — Andrus Intellectual Property Law, LLP

(57) ABSTRACT

A method of taking pulse oximetry measurements on a specific patient and a bracelet-type pulse oximeter device are disclosed. A calibration pulse-oximeter is adapted to estimate one or more first, reference SpO2 values from a first, reference PPG signal measured by the pulse-oximeter on a first, reference area of the human body. Using the same or a different calibration pulse-oximeter, one or more second SpO2 values are estimated from a second PPG signal measured by said same or different calibration pulse-oximeter on a second, target area of the human body. A plurality of third SpO2 values is measured from the second PPG
(Continued)

signal on the second, target area of the human body and the resulting values are calibrated using said calibration parameter or function.

20 Claims, 7 Drawing Sheets

(51) Int. Cl.
*A61B 5/0205* (2006.01)
*A61B 5/024* (2006.01)
*A61B 5/1495* (2006.01)

(52) U.S. Cl.
CPC .......... *A61B 5/681* (2013.01); *A61B 5/02416* (2013.01); *A61B 5/02438* (2013.01); *A61B 2560/0223* (2013.01); *A61B 2562/043* (2013.01)

(56) References Cited

U.S. PATENT DOCUMENTS

| | | |
|---|---|---|
| 2004/0024297 A1 | 2/2004 | Chen et al. |
| 2013/0296670 A1* | 11/2013 | Chen .................. A61B 5/6816 600/323 |
| 2014/0200423 A1 | 7/2014 | Eisen et al. |
| 2015/0366492 A1 | 12/2015 | De Haan et al. |
| 2017/0367599 A1 | 12/2017 | Sanyal et al. |
| 2018/0184923 A1 | 7/2018 | Tal et al. |
| 2018/0206795 A1* | 7/2018 | Al-Ali .................. A61B 5/1455 |

FOREIGN PATENT DOCUMENTS

| | | |
|---|---|---|
| WO | 2016193735 | 12/2016 |
| WO | 2016199124 | 12/2016 |
| WO | 2019193196 | 10/2019 |

OTHER PUBLICATIONS

Forstner "Pulseoximetrie: Stand Und Entwicklung Der Technik" Biomedizinesche Technik, Fachverlag, Schiele und Schoen GmbH, Berlin, Germany, vol. 33, No. 3, published Sep. 10, 1988.
International Search Report and Written Opinion for PCT Application No. PCT/EP2020/078516, mailed Jan. 29, 2021.
Search Report for UK Application No. GB1914632.3, search conducted on Feb. 1, 2021.

* cited by examiner

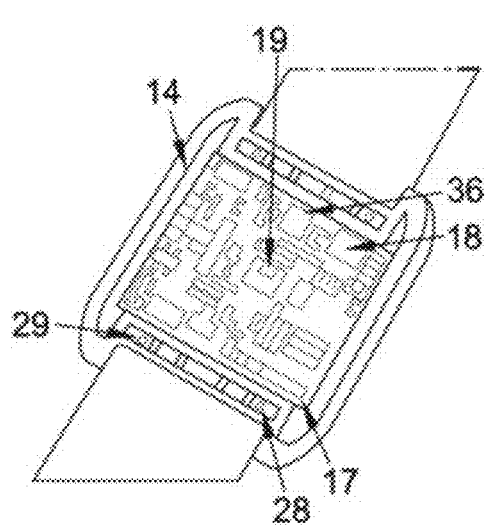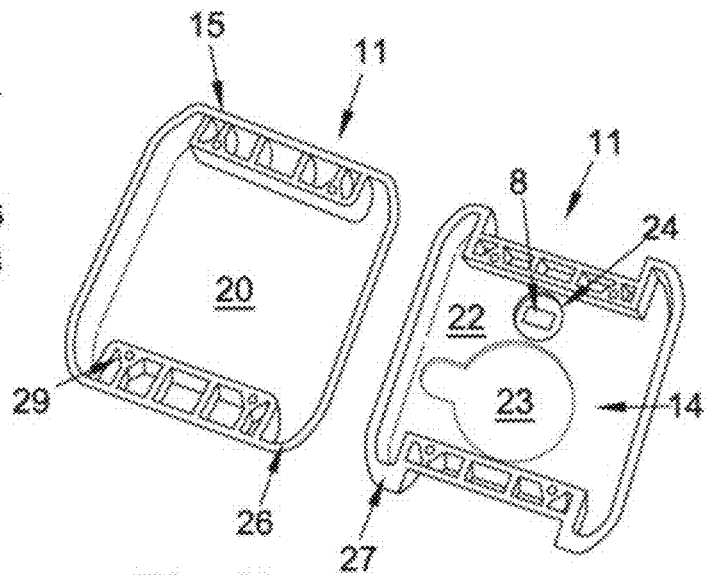
Fig.3a    Fig.3b
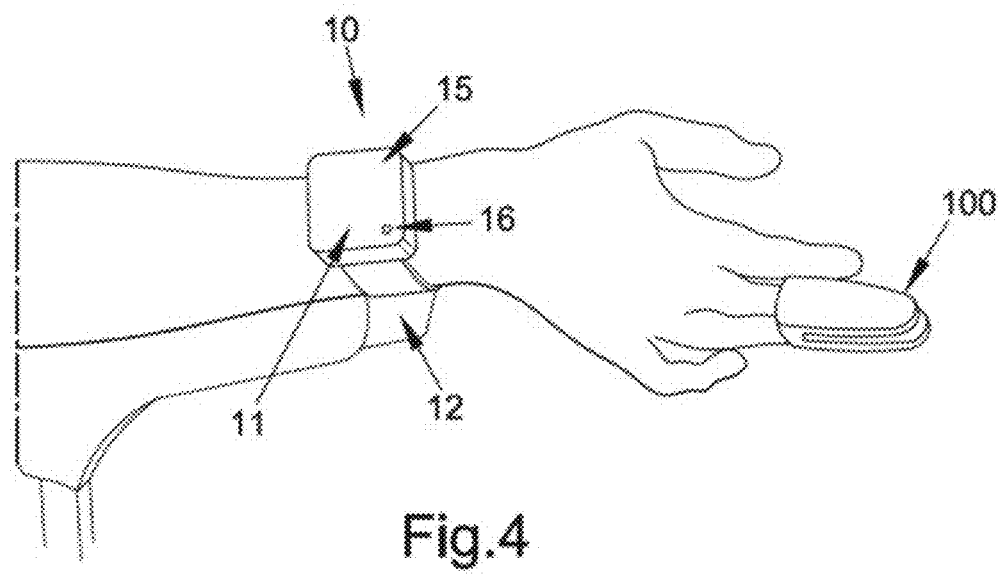
Fig.4

PULSE OXIMETRY METHODS, DEVICES AND SYSTEMS

CROSS-REFERENCE TO RELATED APPLICATIONS

This application is the U.S. national stage application of International Application No. PCT/EP2020/078516, filed on Oct. 9, 2020, which international application was published on Apr. 15, 2021, as International Publication WO 2021/069729 A1 in the English language. The international application is incorporated herein by reference, in its entirety. The international application claims priority from United Kingdom Patent Application No. 1914632.3, filed on Oct. 9, 2019, which is incorporated herein by reference, in its entirety.

TECHNICAL FIELD

The present invention relates to a method of measuring and/or monitoring blood oxygenation. In particular, the present invention relates to a medical method of measuring and/or monitoring blood oxygenation. With medical we mean that the present invention relates to a method of measuring and/or monitoring blood oxygenation that enables medical diagnosis in a subsequent phase, or as a subsequent step, ie after pulse oximetry data have been collected. The present invention, in other words, relates to a medical pulse-oximetry method of collecting heart rate and SpO2 data. The present invention also relates to a device and/or a system for carrying out said method.

BACKGROUND

Medical doctors carry out diagnoses based on biometric data acquired on the human body. Pulse oximetry is a biometric technique that simultaneously measures heart rate and blood oxygenation by estimating oxygen saturation levels in haemoglobin in peripheral arterial blood.

Certain pulse oximetry methods are based on non-invasive detection of light reflected, scattered or otherwise transmitted through a peripheral tissue perfused with blood. These methods are generally collectively referred to as photoplethysmography. Accordingly, a photoplethysmographic signal (or, PPG signal) is collected by at least one PPG sensor, and then analysed. A subclass of these methods relies on the estimation of a blood oxygenation parameter known in literature as "peripheral capillary oxygen saturation" or "SpO2". SpO2 is calculated as the fraction of oxygenated haemoglobin over the total haemoglobin transported by the (peripheral, capillary) blood. The theory shows that this parameter can be linked to certain characteristics of the detected light, as will be described further herein.

The above pulse oximetry methods are preferred over invasive methods which, instead, require access to the blood. Invasive methods measure directly oxygen levels in one or more blood samples, and the corresponding measured parameter is known as "arterial blood oxygen saturation" or "SaO2". Since oxygen is only removed from blood in capillaries, SpO2 can provide an estimate of SaO2. Conveniently, this indirect measurement of SaO2 can be obtained by measuring certain properties of light which has interacted with a peripheral tissue irrorated with blood. Pulse oximetry is recognised as having the potential to provide highly accurate blood oxygenation estimates.

The present application focusses exclusively on methods, and devices and systems for carrying out said methods, of estimating SpO2.

Although SpO2 is calculated from measured characteristics of a detected light, and is therefore in more appropriate terms only estimated, or calculated, to align with terminology more often used in practice in the present application we refer to the estimation or calculation of the SpO2 parameter as the "measurement" of SpO2. However, it will be clear that what the methods, devices and systems described herein actually measure are one or more properties of detected light and then estimate or calculate SpO2 based on these measured properties of the detected light.

SpO2 "measurements" must accurately represent the level of blood oxygenation to be medically relevant, and thus potentially form the basis for medical diagnosis.

A set of SpO2 measurements must also be internally consistent to be medically applicable, so that patterns and trends in the data can be recognised and diagnosis performed.

It is also important to be able to acquire SpO2 measurements on a patient at regular intervals, or at least very frequently throughout a complete periodic time window, for example of the duration of 24 hours, so that the data may encompass different patient conditions related to the patient's everyday life such as sleeping, working, walking and exercising, amongst others.

The above requirements, however, pose various technical challenges.

The measurements may not be accurate (in absolute terms) or may lack consistency (in relative terms). This may be due to intrinsic measurement artefacts introduced, for example, by the respiratory activity of the patient, or by external patient conditions such as, for example, physical exercise.

Patient motion of any kind may in principle displace the sensors or alter their contact with the skin of the subject.

There is also the problem that the measurements may be adversely affected by other patient variables, such as skin elasticity and/or pigmentation, which vary with different patients.

There are also other variables which may adversely affect the repeatability of the measurements (for example, temperature), and many of these are discussed in the literature.

The prior art has attempted to mitigate the above problems.

It is known to perform heart rate measurements using a first pulse-oximeter on the human body, and simultaneously perform SpO2 measurements using a second pulse-oximeter at a nearby location on the same human body using different devices that employ different techniques. Similar artefacts are thus likely to affect the measurements collected from each device. These artefacts can thus be recognised and accordingly their adverse effect on any measurements averaged out, smoothened and/or reduced to improve the accuracy or consistency of the SpO2 measurements.

Patients may be confined to a monitoring space, such as a hospital room, so that the SpO2 measurements can be taken by medical-grade recording apparatus available on site. Such apparatus is certified for medical use and is thus relied upon to provide sufficient accuracy and sufficient consistency for medical diagnosis, at least in these controlled conditions. However, this equipment is only typically available for use in said monitoring spaces, where the patients are under controlled monitoring conditions. Further, the presence of clips and wires connecting the sensors with a central measurement unit makes it difficult to use such apparatus off site.

The above shortcomings could in principle be mitigated by implementing wireless communication. However, the sensors would still need to be provided as part of clip probes, such as finger clip probes or ear clip probes, so that the measurements would still be carried out on portions of the human body such as a finger's tip or an ear's lobe known to be sufficiently perfused with arterial blood. This may in principle lead to medically acceptable measurements.

Clips of any type, however, are not ideal, since they limit the range of activities that the patient can carry out outside the hospital room. For example, a patient wearing a clip probe on a finger, or on an ear lobe, is likely not to behave naturally in his/her workplace or at home, to reduce or eliminate physical exercise, or not to be able to sleep properly. These events may be detrimental to medical diagnosis based on collected SpO2 measurements.

On a different note, non-medical wearable pulse oximeters have been proposed in recent times and it is expected that in due course these devices will become generally increasingly available to the public as lifestyle aids. Some of these wearable devices will include bracelets wearable around the wrist. As such, these devices will be discreet and non-invasive. Whilst the corresponding pulse oximetry *readings* (italicised text is used here to affirm a contrast between blood oxygenation 'readings' in lifestyle devices and blood oxygenation 'measurements' in medical-grade devices via the estimation of the SpO2 parameter; see further the paragraph below) will be generally informative of the user's level of blood oxygenation, and will therefore be used by the device to suggest certain lifestyle actions to the user, or by the user to decide, for example, to change a lifestyle behaviour (for example do more physical exercise, or go to see a doctor), they will very unlikely be medically or clinically acceptable, since a medical doctor would not consider these readings to be appropriate for medical diagnosis, at least in connection with certain conditions which may be difficult to diagnose without accurate, repeatable, consistent, reliable and/or frequently collected data over sufficiently extended periods of time such as a whole 24-hour cycle.

The term *reading* has been used in the paragraph above to denote SpO2 measurements carried out by non-medical devices in a non-medical context and/or for non-medical purposes. This is in contrast with the meaning given herein to terms such as estimate or measurement of SpO2, which instead denote medically relevant SpO2 data gathered using a novel pulse oximetry method using a related device and/or related system.

It is the aim of at least one aspect or at least one embodiment of the presently disclosed pulse oximetry methods, devices and systems to mitigate at least one of the above shortcomings associated with the prior art.

SUMMARY OF THE INVENTION

According to an aspect of the present disclosure, there is provided a method of taking pulse oximetry measurements, the method comprising:
   providing a calibration pulse-oximeter adapted to estimate one or more first, reference SpO2 values from a first, reference PPG signal measured by the calibration pulse-oximeter on a first, reference area of the human body;
   using the same or a different calibration pulse-oximeter, estimating one or more second SpO2 values from a second PPG signal measured by said same or different calibration pulse-oximeter on a second, target area of the human body;
   calculating a calibration parameter or calibration function on the basis of the one or more first, reference SpO2 values and the second SpO2 values; and
   using a measurement pulse-oximeter, measuring a plurality of third SpO2 values from the second PPG signal on the second, target area of the human body, wherein said third SpO2 values are calibrated using said calibration parameter or calibration function.

Preferably, the same calibration pulse-oximeter is used to estimate said first, reference one or more SpO2 values and said second one or more SpO2 values.

Preferably, the second one or more SpO2 values are estimated with the same calibration pulse-oximeter after the first, reference one or more SpO2 values have been estimated.

Preferably, the second one or more SpO2 values are estimated within or after one hour; more preferably within or after half an hour; more preferably within or after 15 minutes; more preferably within or after 10 minutes; more preferably within or after 5 minutes; and, more preferably within or after one minute, than the first, reference one or more SpO2 values have been estimated.

Preferably, said second, target area is located generally around a wrist.

Preferably, said second, target area is located generally on an underside of the wrist.

Preferably, at least one of the calibration pulse-oximeters and the measurement pulse-oximeter is a bracelet-type pulse-oximeter.

Preferably, the measurement pulse-oximeter is a bracelet-type pulse-oximeter.

Preferably, the calibration and measurement pulse-oximeters are the same bracelet-type pulse-oximeter.

Preferably, the first, reference area of the human body has greater blood perfusion than the second, target area of the human body.

Preferably, the first, reference area of the human body is a fingertip or an ear lobe.

Preferably, the calibration parameter or function is calculated from a single or single-acquired first, reference SpO2 value and/or from a single or single-acquired second SpO2 value.

Preferably, the calibration parameter is an offset calculated as a difference between a single or single-acquired (that is, 'acquired once') first, reference SpO2 value and a single or single-acquired (that is, 'acquired once') second SpO2 value.

Preferably, the calibration pulse-oximeter(s) and the measurement pulse oximeter are each adapted to derive a same mathematical parameter from respectively the first, reference PPG signal and the second PPG signal.

Preferably, the calibration pulse-oximeter used for estimating said first, reference one or more SpO2 values is a medical-grade pulse-oximeter; preferably, a medically certified pulse-oximeter.

Preferably, the calibration pulse-oximeter used for estimating said first, reference one or more SpO2 values comprises one or more wires for transmitting signals from at least one pulse oximetry probe to a central measurement unit.

Preferably, said pulse oximetry probe is a finger probe or ear lobe probe.

Preferably, the calibration pulse-oximeter(s) and the measurement pulse-oximeter comprise at least one light emitter and at least one light detector adapted to detect light emitted by said light emitter after the light has passed through a human tissue.

Preferably, the light detector is adapted to measure a light intensity.

Preferably, said pulse-oximeters each comprise two light emitters for emitting two respective substantially monochromatic lights at different wavelengths; preferably, wherein said different wavelengths comprise a red wavelength and an infrared wavelength.

Preferably, the mathematical parameter derived from the first, reference PPG signal and/or the second PPG signal is a parameter R calculated as follows:

$$R = \frac{RedAC/RedDC}{InfraRedAC/InfraRedDC},$$

wherein,

RedAC is an AC component of the light having the red wavelength;

RedDC is a DC component of the light having the red wavelength;

InfraRedAC is an AC component of the light having the infrared wavelength; and,

InfraRedDC is a DC component of the light having the infrared wavelength.

Preferably, the method further comprises:
 storing the calibration parameter or calibration function in a memory provided in the measurement pulse-oximeter.

Preferably, the bracelet-type pulse-oximeter comprises a case and a strap;
 wherein the case accommodates a pulse oximetry unit comprising:
  two light emitters for emitting substantially monochromatic lights at different wavelengths comprising a red wavelength and an infrared wavelength; and,
  a light detector;
 and wherein the strap comprises:
  a flexible elongated element connected to the case.

According to another aspect, the present disclosure provides a bracelet-type pulse oximetry device for measuring blood oxygenation on a wrist of a user/patient, the device comprising:
 one or more light emitters adapted to emit light directed into said wrist and from there into a human tissue;
 at least one light detector for detecting said light after the light has passed through said human tissue;
 wherein the device is adapted to convert one or more measured characteristics of the detected light into corresponding SpO2 measurements,
 wherein said SpO2 measurements are calibrated according to a calibration parameter or calibration function previously obtained in accordance with the following method:
  providing a calibration pulse-oximeter adapted to estimate one or more first, reference SpO2 values from a first, reference PPG signal measured by the calibration pulse-oximeter on a first, reference area of the human body;
  using the same or a different calibration pulse-oximeter, estimating one or more second SpO2 values from a second PPG signal measured by said same or different calibration pulse-oximeter on said wrist;
  calculating the calibration parameter or the calibration function on the basis of the one or more first, reference SpO2 values and the one or more second SpO2 values.

Preferably, said device is adapted to measure a light intensity; or, said one or more measured characteristics comprise a light intensity.

Preferably, the device further comprises two light emitters for emitting two respective substantially monochromatic lights at different wavelengths.

Preferably, said different wavelengths comprise a red wavelength and an infrared wavelength.

Preferably, the device is adapted to calculate a mathematical parameter R as follows:

$$R = \frac{RedAC/RedDC}{InfraRedAC/InfraRedDC},$$

wherein,

RedAC is an AC component of the light having the red wavelength;

RedDC is a DC component of the light having the red wavelength;

InfraRedAC is an AC component of the light having the infrared wavelength; and,

InfraRedDC is a DC component of the light having the infrared wavelength; and, wherein the device is adapted to measure SpO2 as a function of said parameter R.

Preferably, the light detector is adapted to detect light reflected towards the device.

Preferably, the device comprises a memory and the calibration parameter or calibration function are stored locally on said memory.

Preferably, the device comprises a bracelet and a case, wherein the case accommodates the one or more light emitters and the at least one light detector.

Preferably, said case includes said memory.

Preferably, said case further comprises a processor programmed to perform said measurement of the one or more characteristics of the detected light and to perform said conversion and calibration.

According to another aspect, the present invention provides a system comprising, in combination, a device as described herein and a docking station for docking the device thereto, wherein the device and the docking station are operable to exchange data therebetween.

Preferably, the docking station is adapted to wirelessly recharge the device.

Preferably, the docking station incorporates the calibration pulse-oximeter(s) and the measurement pulse-oximeter.

Preferably, the calibration and measurement pulse-oximeters, and said device, are one and the same pulse-oximeter.

According to yet a further aspect of the present disclosure, there is provided a method of measuring blood oxygen levels using a bracelet-type pulse oximetry device, the method comprising:
 providing a pulse oximetry device as described herein, or a system as described herein;
 applying the device to the wrist of a test subject/patient such that the one or more light emitters are adapted to emit light into an underside of the wrist, and such that the at least one light detector detects reflected light from the wrist underside;

measuring one or more characteristics of the detected light which can be converted into corresponding SpO2 measurements;

converting said measured one or more characteristics into said SpO2 measurements;

wherein said SpO2 measurements are calibrated according to a calibration parameter or a calibration function obtained in accordance with the following method:

providing a calibration pulse-oximeter adapted to estimate one or more first, reference SpO2 values from a first, reference PPG signal measured by the calibration pulse-oximeter on a first, reference area of the human body;

using the same or a different calibration pulse-oximeter, estimating one or more second SpO2 values from a second PPG signal measured by said same or different calibration pulse-oximeter on the wrist underside of the test subject/patient;

calculating the calibration parameter or the calibration function on the basis of the one or more first, reference SpO2 values and the second SpO2 values.

Preferably, applying the device to the wrist underside comprises identifying at least one position of the device relative to the wrist underside which optimises and/or maximises a signal to noise ratio in relation to a PPG signal that represents said measured characteristics of the detected light.

Preferably, applying the device to the wrist underside comprises marking the wrist with reference markers for positioning the device relative to the wrist.

Preferably, applying the device to the wrist underside comprises affixing one side of a double-sided adhesive element around a protrusion provided on a backside of the device, wherein said protrusion is arranged to cooperate with the one or more emitters and the at least one detector for emitting and detecting said light and to grip the wrist underside.

Preferably, applying the device to the wrist underside comprises affixing the device to the wrist via the other side of the double-sided adhesive element.

According to a further aspect of the present disclosure, there is provided a pulse oximetry device for measuring blood oxygenation, the device comprising:

a bracelet-type pulse oximeter for acquiring blood oxygenation measurements on a wrist of a user/patient, wherein the pulse oximeter comprises:

a case and a bracelet adapted such that a face of the case may be disposed in contact with an underside of said wrist when the pulse oximeter is worn by the user/patient, and wherein the case comprises:

a plurality of pulse oximetry sensing units arranged in a spatially distanced configuration on said face of the case of the pulse oximeter;

wherein each of said sensing units comprises at least one light emitter adapted to emit light into the wrist underside and from there into a human tissue, and at least one light detector for detecting light reflected from the wrist;

wherein each sensing unit is adapted to measure at least one photoplethysmographic (PPG) signal during a measurement interval, and the device is adapted to convert said measured PPG signal into a respective SpO2 measurement;

wherein each pulse oximetry sensing unit of the pulse oximeter is calibrated according to a respective, sensing unit-specific calibration parameter or calibration function obtained in accordance with the following method:

using a calibration pulse-oximeter, estimating one or more first, reference SpO2 values from a first, reference PPG signal measured by the calibration pulse-oximeter on a first, reference area of the human body;

using the bracelet-type pulse oximeter, estimating one or more second SpO2 values from a second PPG signal measured by a respective pulse oximetry sensing unit on the wrist underside, wherein the first, reference area of the human body has greater blood perfusion than the wrist underside;

calculating said respective, sensing unit-specific calibration parameter or calibration function on the basis of the one or more first, reference SpO2 values and the one or more second SpO2 values.

Preferably, each light detector is adapted to measure a light intensity.

Preferably, each pulse oximetry unit comprises two light emitters for emitting two respective substantially monochromatic lights at different wavelengths.

Preferably, each pulse oximetry unit comprises three light emitters for emitting three respective substantially monochromatic lights at different wavelengths.

Preferably, said different wavelengths comprise at least one of a red wavelength or a green wavelength, and an infrared wavelength.

Preferably, said different wavelengths comprise a red wavelength, a green wavelength and an infrared wavelength.

Preferably, the device or the bracelet-type pulse oximeter is adapted to calculate for each sensing unit at least one sensing unit-specific mathematical parameter R as follows:

$$R = \frac{RedAC/RedDC}{InfraRedAC/InfraRedDC},$$

$$\text{or } R = \frac{GreenAC/GreenDC}{InfraRedAC/InfraRedDC},$$

wherein,

RedAC is an AC component of the light having the red wavelength;

RedDC is a DC component of the light having the red wavelength;

GreenAC is an AC component of the light having the green wavelength;

GreenDC is a DC component of the light having the green wavelength;

InfraRedAC is an AC component of the light having the infrared wavelength;

InfraRedDC is a DC component of the light having the infrared wavelength.

The device (or the bracelet-type pulse oximeter) are preferably adapted to convert for each sensing unit the measured PPG signals into the respective SpO2 measurement as a function of said parameter R. In other words, it is preferably that the device/pulse oximeter convert R into SpO2 for each pulse oximetry sensing unit.

Preferably, the bracelet-type pulse oximeter comprises a memory and the calibration parameters or calibration functions are stored locally on said memory. Alternatively, the memory may be provided as part of the device, and the calibration parameters or calibration functions may be provided on that memory.

Preferably, the device comprises a processor programmed to perform said calibration and/or conversion. Preferably, said processor is provided as part of the bracelet-type pulse oximeter.

Preferably, the processor is programmed to associate to each measured PPG signal at least one score representative of measurement quality during the measurement interval, and wherein the processor is programmed to carry out said conversion considering said scores.

Preferably, the bracelet-type pulse oximeter comprises an accelerometer and at least one of said scores is inversely related to a first correlation factor between a signal output by the accelerometer during the measurement interval and the PPG signal measured during the measurement interval.

Preferably, at least one of said scores is directly related to a second correlation factor between the PPG signal measured during the measurement interval and a comparison signal obtained as an average of other PPG signals.

Preferably, at least one of said scores is determined based upon a time domain analysis of the PPG signal.

Preferably, said at least one of said scores is determined based upon a repeatability of peak-to-peak amplitudes of the PPG signal during the measurement interval.

Preferably, said at least one of said scores is determined based upon absolute values of peak-to-peak amplitudes and/or an absolute value of the mean amplitude of the PPG signal during the measurement interval.

Preferably, at least one of said scores is determined based upon a frequency domain analysis of the PPG signal.

Preferably, at least one of said scores is determined based upon an analysis of a spectrum, such as a power spectrum, of the PPG signal.

Preferably, at least one of said scores is determined based upon a spectral skewness and/or a spectral standard deviation around a main frequency of said spectrum of the PPG signal.

It is possible to adopt the same scoring strategy for all measured PPG signals, or to adopt different scoring strategies for different PPG signals.

It is also possible to apply all scoring strategies for each of the measured PPG signals, and assign to each measured PPG signal a mean score based upon an average of all the scores applied to that PPG signal.

Preferably, said conversion is based upon a weighted average of the SpO2 measurements measured by each pulse oximetry sensing units.

Said weighted average may be based upon weights that are proportional to said scores or mean scores.

Preferably, the processor is programmed to exclude from said conversion one or more measured PPG signals based upon said scores, for example if said one or more PPG signals score below a pass threshold.

Preferably, the processor is programmed to increase the intensities of the emitted lights that generate one or more PPG signals having scores higher than the scores of other PPG signals, relative to the intensities of the other emitted lights.

Preferably, the processor is programmed to decrease the intensities of the emitted lights that generate one or more PPG signals having scores lower than the scores of other PPG signals, relative to the intensities of the other emitted lights.

Preferably, the processor is programmed to calculate an average measured PPG signal for each colour of light emitted by the light emitters, and to perform said conversion based upon said one or more average measured PPG signals.

Preferably, the bracelet-type pulse oximeter comprises three pulse oximetry units disposed in a triangular configuration, that is as opposed to having three pulse oximetry units disposed on, or substantially on, a straight line. However, it may be advantageous to provide the three pulse oximetry units in a substantially linear configuration, which may preferably be in the direction of the bracelet. When the device is in use, this is therefore generally transversally with respect to a direction of an ulnar artery.

Preferably, the bracelet-type pulse oximeter comprises four pulse oximetry units disposed in a quadrilateral configuration, which may increase an area delimited by a nominal polygon whose vertices correspond to the pulse oximetry units. However, it may be advantageous to provide the four pulse oximetry units in a substantially linear configuration, or in a T-shaped configuration, or in a Y-shaped configuration, or in an L-shaped configuration. When the device is in use, and the units are disposed in linear configuration, this is preferably generally transversally with respect to a direction of an ulnar artery.

For the same reasons, or to increase the number of measurement points in space on the wrist underside, preferably the bracelet-type pulse oximeter comprises five or six pulse oximetry units, which may be disposed in a pentagonal or hexagonal configuration, respectively. More sensing units may be desirable, but the space available on the face of the pulse oximeter may be limited. However, it may be advantageous to provide the five or six pulse oximetry units in a substantially linear configuration, or in a T-shaped configuration, or in a Y-shaped configuration, or in an L-shaped configuration, or in a star-shaped configuration, or in a cross-shaped configuration. When the device is in use, and the units are disposed in linear configuration, this is preferably generally transversally with respect to a direction of an ulnar artery.

According to yet another aspect of the present disclosure, there is provided a system comprising, in combination, a device as described herein, which device may be constituted only by a bracelet-type pulse oximeter as described herein, and a docking station for docking the bracelet-type pulse oximeter thereto, wherein the bracelet-type pulse oximeter and the docking station are operable to exchange data therebetween;
- optionally, wherein the docking station is adapted to wirelessly recharge the bracelet-type pulse oximeter;
- optionally, wherein the docking station incorporates the calibration pulse-oximeter;
- preferably, wherein the calibration pulse oximeter is the same bracelet-type pulse oximeter.

According to yet another aspect of the present disclosure, there is provided a method of calibrating a pulse oximetry device as described herein, the method comprising:
- disposing the bracelet-type pulse oximeter around the wrist of the user/patient such that said face of the case of the bracelet-type pulse oximeter is in contact with the wrist underside;
- using a calibration pulse-oximeter, estimating one or more first, reference SpO2 values from a first, reference PPG signal measured by the calibration pulse-oximeter on a first, reference area of the user/patient;
- using the bracelet-type pulse oximeter, estimating one or more second SpO2 values from a second PPG signal measured by one of the pulse oximetry sensing units on the wrist underside, wherein the first, reference area of the user/patient has greater blood perfusion than the wrist underside;

calculating a respective, sensing unit-specific calibration parameter or calibration function on the basis of the one or more first, reference SpO2 values and the one or more second SpO2 values;

repeating said estimating and calculating for each of the pulse oximetry sensing units thereby obtaining a set of respective calibration parameters or calibration functions, one for each respective pulse oximetry sensing unit.

According to yet another aspect of the present disclosure, there is provided a method of measuring SpO2 on a wrist underside of a user/patient using a pulse oximetry device as described herein, the method comprising:

disposing the bracelet-type pulse oximeter around the wrist of the user/patient such that said face of the case of the bracelet-type pulse oximeter is in contact with the wrist underside;

using the plurality of pulse oximetry sensing units, acquiring PPG signals representative of spatially distanced locations on the wrist underside during a measurement interval; and, converting said PPG signals into a measured SpO2 value for the user/patient for said measurement interval.

According to yet a further aspect of the present invention, there is provided a computer programme product comprising a computer readable medium comprising computer readable instructions stored thereon for performing a method as described herein.

Any features described above in connection with any one or more of the aspects of the present disclosure may be included or combined with the features described in connection with any one or more of the other aspects of the present disclosure, unless specifically stated otherwise.

The invention will now be described, purely by way of example, in connection with the attached drawings in which:

DRAWINGS

FIG. 3a is a front perspective view of the pulse oximetry device of FIGS. 1 and 2 with an upper portion of a case removed to reveal a printed circuit board (PCB) that is used to control the device;

FIG. 3b shows the internal faces of the upper and lower portions of the case of the pulse oximetry device of FIGS. 1-3, with the PCB and other components removed;

FIG. 4 shows the pulse oximetry device of FIGS. 1-3 during a calibration procedure that utilises a known medical grade pulse-oximeter with a finger clip probe as a reference instrument;

FIG. 5a shows the underside of the PCB of FIG. 3a;

Figure 7:
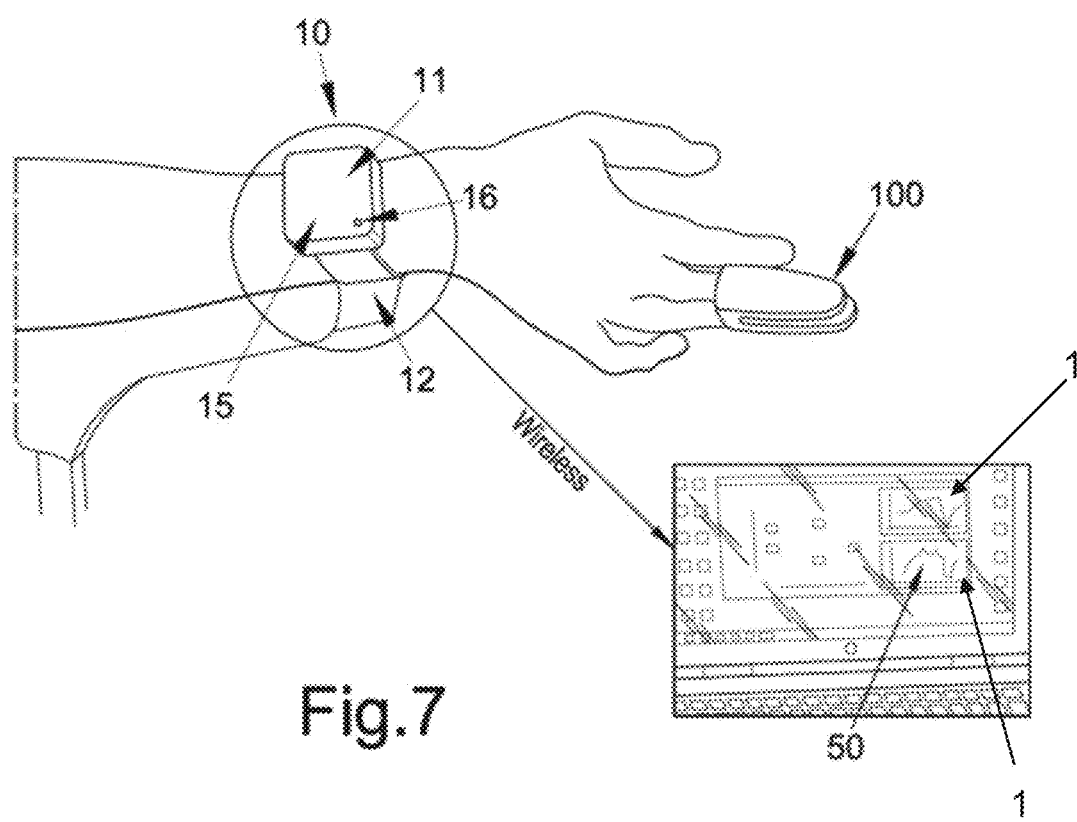
FIG. 7 illustrates a process of monitoring blood oxygenation levels on a patient based on acquisition of PPG signals.
Figure 10:
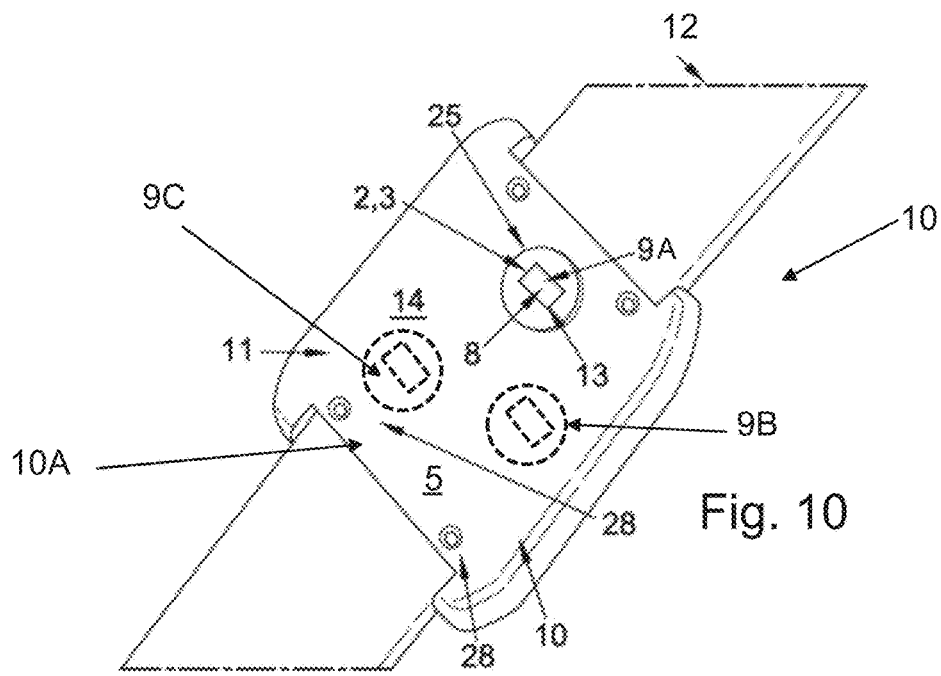
Figure 11:
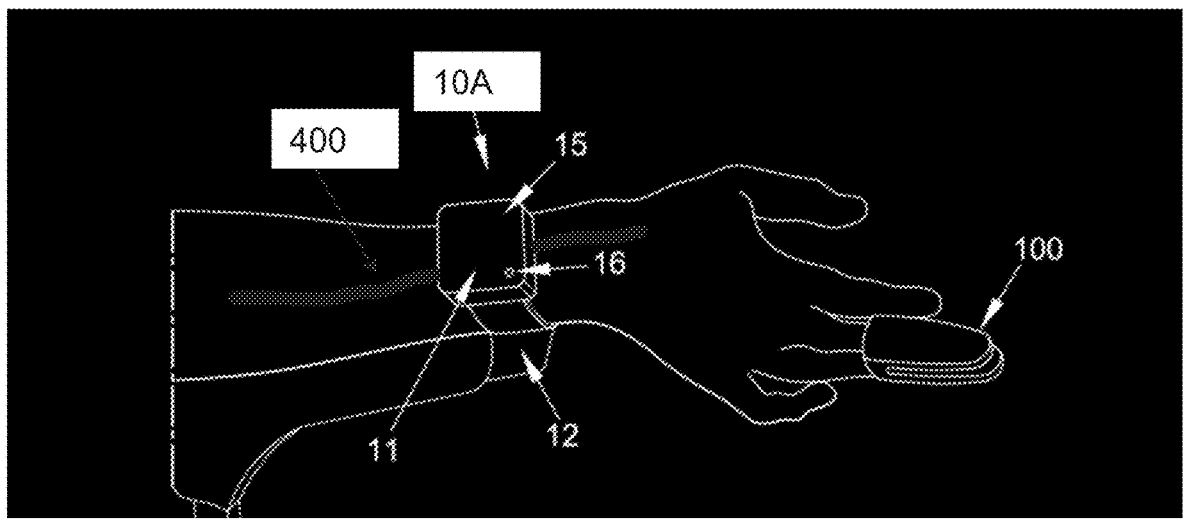

FIG. 10 is a rear perspective view of yet a further pulse oximetry device, similar to that of FIGS. 1-3 and 5, comprising multiple pulse oximetry sensing units; and, FIG. 11 shows the pulse oximetry device of FIG. 10 during a calibration procedure similar to that illustrated by FIG. 4—or during a process of monitoring blood oxygenation levels on a patient akin to that shown by FIG. 7—with the location of an ulnar artery schematically illustrated.

DESCRIPTION

The inventors have appreciated the advantages of providing upgraded pulse oximetry devices similar to wearable pulse oximetry devices which are soon to become commercially wide spread but adapted to gather medically relevant pulse oximetry data frequently and over extended periods of time, such as full 24-hour cycles, or longer.

The adaptation essentially consists in calibrating such instruments against one or more trusted measurements taken in areas of the human body with a higher level of blood perfusion than the areas on which such instruments are designed to operate, and typically a wrist (but preferably in relation to the methods described herein on a wrist underside). In other words, the inventors have appreciated that it may be acceptable to measure SpO2 on areas of relatively low blood perfusion (such as the wrist, and more particularly the wrist underside), in as far as these measurements are corrected/calibrated based upon one or more previous measurements taken on areas of higher blood perfusion, which are deemed to provide accurate medical measurements, that is measurements that then enable medical diagnosis.

The inventors have shown that their unique calibration methodology enables the gathering of more meaningful SpO2 data. Accordingly, it is expected that medical doctors will be able to use these improved data sets to diagnose more easily and/or more reliably conditions which until now have been difficult to diagnose, or that have not been possible to diagnose using conventional pulse oximetry.

The inventors have also improved mechanical aspects of certain wearable pulse oximetry devices, so that these improved devices can maintain a natural, yet appropriate, interface with the measurement area which is desirably designated as a back-face or the underside of the wrist of a patient (location opposite to that of traditional watches).

Figure 1:
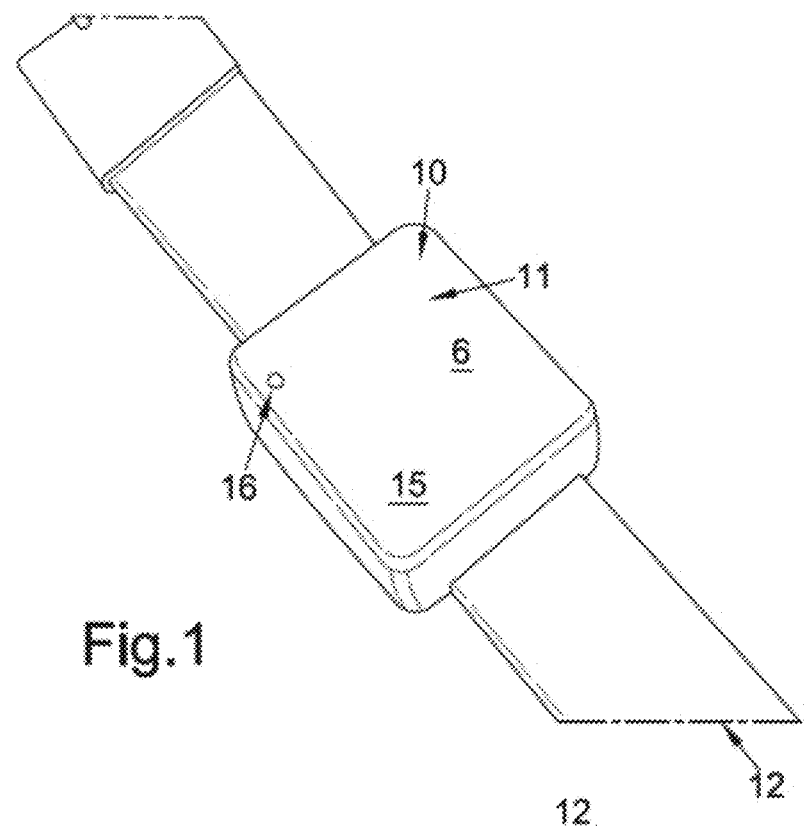
FIG. 1 is a front perspective view of a pulse oximetry device as described herein.

FIG. 1 shows a pulse oximetry device 10 capable of accurately and consistently monitoring levels of oxygen saturation in haemoglobin transported by peripheral arterial blood in a patient—a parameter known from the literature as SpO2.

The pulse oximetry device 10 frequently acquires and monitors medically relevant SpO2 data over relatively large time periods, for example of the duration of 12 or 24 hours.

As used herein, "monitoring" refers to the activity of repeatedly "measuring" and then saving, displaying or otherwise keeping record of SpO2 data over a protracted period of time so as to reveal any trends or patterns. The SpO2 is measured preferably at regular and relatively small time intervals, for example many times per second, or every second, every five or ten seconds, over a period of for example of 12 or 24 hours, as discussed above.

The underlying signal (and preferably signals) measured by the pulse oximetry device 10 described herein is known in literature as photoplethysmographic signal or, in short, PPG signal. The PPG signal expresses absorption of light that passes through a tissue perfused with arterial blood as a function of time. This depends by a local change in blood volume over time as determined by the systolic and diastolic heart phases. Accordingly, the PPG signal is a generally cyclical waveform and SpO2 is estimated from this periodic signal. The PPG signal can be viewed and analysed in the time and/or frequency domains. It has DC and AC components. Details relating to the PPG signal are not the focus of the present application and will therefore not be described herein in extensive detail. However, it is noted that the PPG signal is, for the purposes of the present disclosure, the base signal which is made available to the pulse oximetry device 10 by one or more appropriate pulse oximetry sensing units 9, one of which is visible in FIG. 2. In particular, the pulse oximetry device 10 described herein uses a light detector 13 as part of such a pulse oximetry sensing unit 9 to detect light intensity.

As is the case more generally with all analogue signals made available by any analogue sensors, the analogue PPG signal detected by the light detector 13 embedded in the pulse oximetry device 10 is sampled and converted into the digital domain according to a predetermined sampling rate. The level of granularity of the acquired data will not be further discussed herein. Instead, the digitally acquired waveforms will simply be treated and referred to herein as one or more signal acquisitions. SpO2 can be measured each time over one or more acquisitions, of variable time duration, during a measurement interval.

Before SpO2 is extracted, the acquisition(s) can be conditioned according to one or more known techniques such as filtering, averaging or the like. Some desired and useful techniques are further described below. In the meantime, it is noted that SpO2 can be extracted more or less frequently from acquisitions having different duration, that is during measurement intervals of variable duration, and that may be conditioned according to different techniques. For example, the PPG signal may be acquired over 10 seconds, after different intervals, and averaged within these acquisition windows. Otherwise, the PPG signal may be acquired over moving windows of 10 seconds and filtered within these windows. A corresponding SpO2 measurement can then be performed by the device 10. Alternative processing methods are however possible. Further, the signals can equally be processed in the time and/or frequency domains, as convenient.

The SpO2 measurements described herein are derived from one or more measured physical parameters. In the present description, SpO2 is estimated from a measured intensity of light that has not been absorbed by oxygenated blood and which, therefore, can complete its travel to the light detector 13. The light absorbed by oxygenated blood relates directly to the quantity of oxygen transported by the blood. If all the haemoglobin transported by the blood transports oxygen, then SpO2 is equal to 100%.

As mentioned above, the quantity or volume of blood (and, with it, of haemoglobin) at any one time present in an area of the human body made the target of the SpO2 measurements generally cycles in time depending on the heart cycles and is therefore related to the heart rate. Generally, however, the blood volume present in the target area at any given time also depends from various other biometric parameters (for example breathing rate or body temperature) or patient conditions (for example physical activity), etc. It is for these reasons—in combination with a weaker PPG signal—that the measurement of SpO2 at the wrist is a challenge, which the present inventors have addressed.

Returning now to the device 10 of FIG. 1, the device 10 can essentially be described as a pulse oximetry bracelet or bracelet-type pulse oximeter 10A that includes a case 11 and a strap 12. The case or housing 11 accommodates one or more pulse oximetry sensing units 9 (just one, in the presently described example) which, as discussed above, in the presently described examples includes a light detector 13. The case 11 is divisible in two parts, of which the front portion 15 is that visible in FIG. 1. A red LED light 16 extrudes from the front face 6 of the case 11, and, as it will be explained in further detail below, provides visual feedback to the patient. As it will be appreciated, the device 10 is very similar at least in shape to a traditional watch. However, the case 11 may be worn on the underside (or back-face) of the wrist, in position circumferentially substantially opposite to that of a traditional watch.

Figure 2:
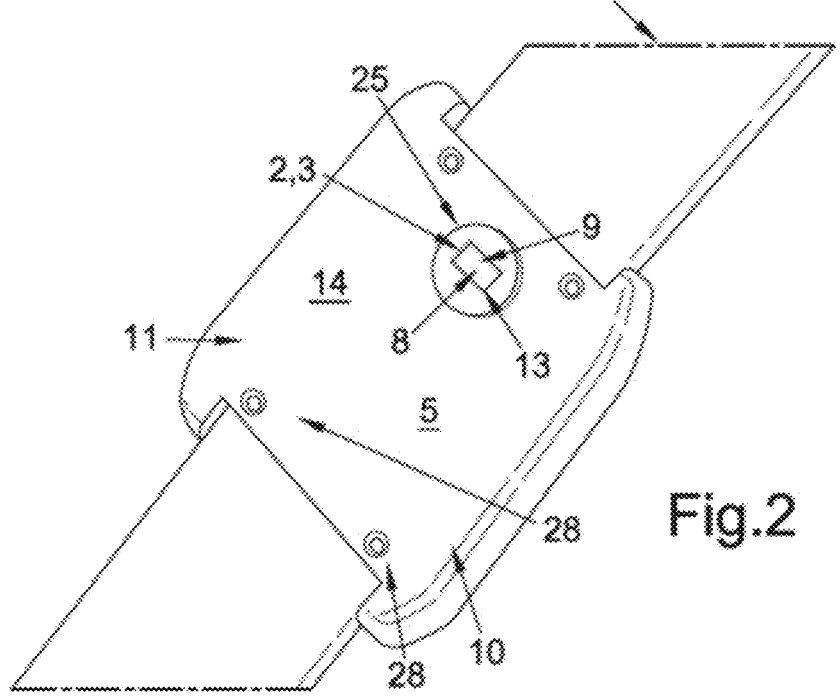
FIG. 2 is a rear perspective view of the pulse oximetry device of FIG. 1.

FIG. 2 shows the rear portion 14 of the case 11. The light detector 13 is disposed on the rear face 5 of the case 11 as shown in FIG. 2. The light detector 13 is associated, in the described pulse oximetry device 10, to two light sources 2, 3 adapted to illuminate the skin of the patient subject to the tests. However, pulse oximetry sensing units 9 with just one light source or more than two light sources 2, 3 are also possible, for example there are currently available from the market pulse oximetry sensing units 9 with three light sources, which may be a red, a green and an infrared light sources. The light detector 13 is adapted to pick up light reflected or scattered back to the device 10 after the light has travelled through the wrist of the patient at depths of typically a few millimetres.

FIG. 3a reveals details of a printed circuit board (PCB) 17 housed in the case 11. The PCB 17 includes various modules that enable the pulse oximetry device 10 to perform different functions. As also seen in FIG. 3a, a memory 18 and a processor 19 are integrated on the PCB 17. The PCB 17 thus manages the acquisition of the PPG signal from the light detector 13 from which the SpO2 is estimated as further described below. It will be understood that although it is particularly convenient to have the PCT 17, and/or the memory 18 and processor 19, onboard the pulse oximetry bracelet 10A, alternatively these elements could be provided externally with the bracelet 10A only performing a signal pick-up function.

Figure 5A:
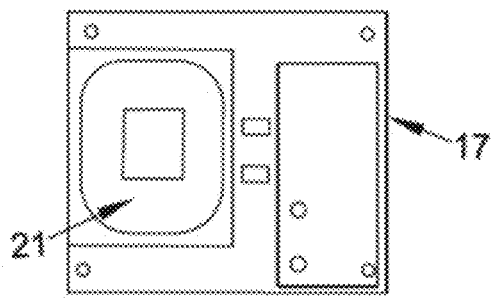

FIG. 3b shows the front and rear portions 14, 15 of the case 11 one next to the other to reveal additional constructive details of the case 11. The front portion 15 of the case 11 has an inner side or face 20 that faces, in use, the PCB 17. The rear portion 14 of the case 11 is instead profiled to accommodate and support a recharge coil 21 (shown in FIG. 5a). In particular, an inner face or side 22 of the rear portion 14 of the case 11 comprises a first recess 23 shaped to conform to this coil 21. The recharge coil 21 is mounted on the rear side of the PCB 17 as shown in FIG. 5a. A second recess 24 is also identifiable on said inner face or side 22 of the case 11. This recess 24 when seen from outside defines a projection 25 of the underside 5 of the case 11 that projects to contact the skin on the wrist of the patient, as shown in FIG. 4. The recess 24 accommodates the pulse oximetry module or unit 9 that comprises the light detector 13 and the light sources 2, 3. The external projection 25 has a window 8 adapted to transmit light therethrough, as shown in FIG. 2.

The pulse oximetry unit 9 mounted on the device 10 is, in the described pulse oximetry device 10, type MAX30102 manufactured by Maxim Integrated, Inc. However, in alternative devices 10 different pulse oximetry units 9 may be used, for example provided by different makers, or having different light emitter and/or sensor configurations, different lighting colours, a different number of lights etc. Further, as it will be described herein, it is also possible and desirable to integrate into the case 11 of the bracelet-type pulse oximeter 10A multiple pulse oximetry sensing units 9.

Another characteristic of the described device 10 is that the device 10 is battery-operated. However, the battery has not been shown in the drawings for clarity purposes, so that other components are better visible. The battery will not be described further.

As will be appreciated, power consumption of this type of devices 10 is minimal. The light sources or emitters 2, 3 embedded in the pulse oximetry unit 9 are LED type and emit red and infrared lights of wavelengths of approximately 600 and 900 nm, respectively.

The projection 25 optimises the contact between the device 10 and the skin of the subject at the wrist, when the device 10 is in use or is being calibrated, as shown in FIG. 4 and as further described below. The protrusion 25 in other words is capable of locally increasing the force and pressure exchanged between the wrist and the case 11, so as to provide additional grip and stability.

Figure 5B:
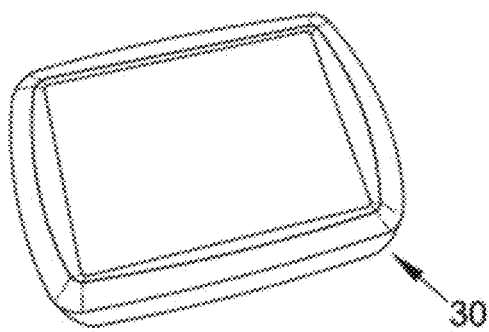
FIG. 5b shows a docking station for the pulse oximetry device of FIGS. 1-4.
Figure 5C:
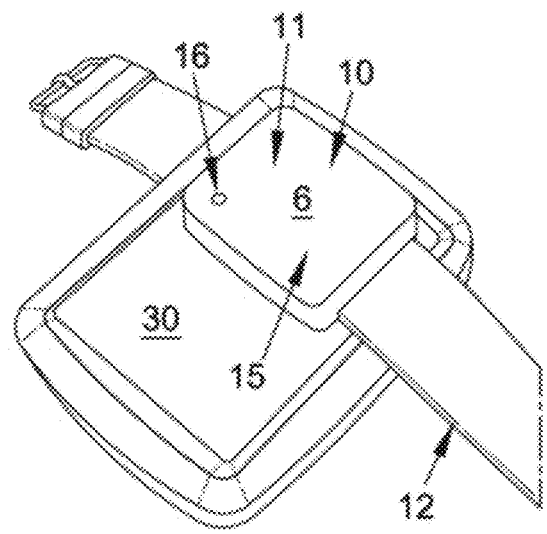
FIG. 5c shows the pulse oximetry device docked to the docking station of FIG. 5b.
Figure 6:
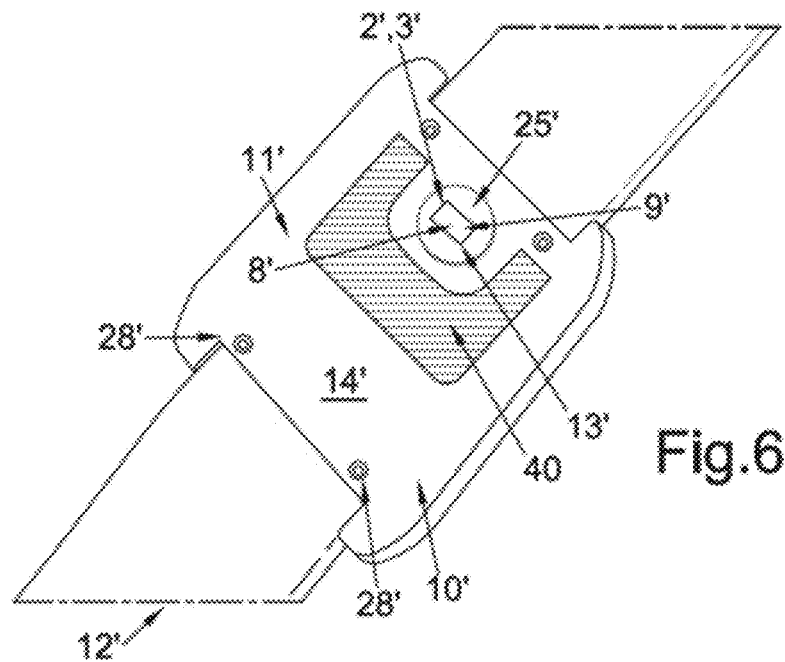
FIG. 6 is a rear perspective view of a second pulse oximetry device having a friction insert.

The pulse oximetry device 10' of FIG. 6 is similar to that shown in FIGS. 1-3 except that it in addition incorporates a rubber insert 40 on the rear face 5' of the lower part 14' of the case 11'. This makes the device 10' less likely to become displaced on the target measurement area. Accordingly, this arrangement provides improved contact between the projection 25' of the device 10' and the wrist of the patient. This improves the consistency of the SpO2 measurements. Numerals corresponding to the numerals adopted in FIGS. 1-5 have been adopted in connection with this pulse oximetry device 10', with the addition of an apex to denote equivalent features described in connection with the earlier device. The rubber insert could alternatively be a double sided adhesive element which is first installed on the device, then attached to the skin.

The device 10 is water proof and this property is provided by water proofing matching profiles 26, 27 of the upper and lower portions 15, 14 of the case 11, and by their connection by means of four screws 28 disposed on the rear face 5 of the lower portion 14 of the case 11 which are used to close the two parts 14, 15 of the case 11, as shown in FIG. 2. However, it will be appreciated that in other devices not described herein in detail these constructive particulars may change. These screws 28 are coupled to appropriate bores 29 provided on the inner face 20 of the upper portion 15 of the case 11, as shown in FIG. 3b. Corresponding screws 28' are also visible in the device 10' shown in FIG. 6.

The PCB 17 can communicate any data stored in the memory 18 via a Bluetooth wireless module (also not shown). The data can be transferred to a docking station 30, a personal computer and/or to the Cloud, depending on the application. In preferred applications, SpO2 measurements gathered by the pulse oximetry device 10 are stored in the memory 18 and periodically downloaded to the docking station 30. The docking station 30 then periodically downloads the data to a personal computer or the Cloud. FIGS. 5b and 5c show the docking station 30 for use with the device 10. The docking station 30 is in addition used to recharge wirelessly the onboard battery via the recharge coil 21, as known in the arts. Preferred docking stations (not shown) incorporate the reference pulse-oximeter 100, which is used to calibrate the main pulse oximetry device 10 as described herein.

The described pulse oximetry device 10 also includes a triaxial accelerometer 36 (see FIG. 3a) which can track movements of the patient to infer patient's behaviour. In the described pulse oximetry device 10, the accelerometer has a 10-bit vertical resolution and is manufactured by NXP Semiconductors. Alternative models and makes would however be possible.

In addition to SpO2, the device 10 is capable of measuring heart rate (also from the PPG signal). Using the accelerometer 36 and the information on the heart rate it would be possible, for example, to estimate a distance walked by the subject, according to algorithms known in the art but not described herein.

Alternatives or additions to the accelerometer 36 are possible, for example in the form of a GPS system which could be fitted to the device 10. The device 10 could thus not only recognise basic events such as 'patient walking' or 'patient jogging', but it could also further characterise the activity of the subject wearing the device 10, for example on the basis of GPS coordinates. Accordingly, the wearable pulse oximetry bracelet 10 described herein not only can record oxygen desaturation events, but it can also quantify their duration and intensity in relation to the activity of the subject.

The processor (or microcontroller) 19 oversees the overall functioning of the device 10. In particular, the processor/microcontroller 19 will:

1) Trigger the emission of light from the light emitters 2, 3—this will ensure the presence of a PPG signal;
2) Acquire the PPG signal, which, as discussed above represents a light intensity and which, in the present description, represents the intensity of light reflected back to the pulse oximetry unit 9 and detected by the light detector 13 ('reflection mode');
3) Condition the PPG signal, if necessary and/or as prescribed;
4) Calculate SpO2 on the basis of the PPG waveform or waveforms captured by the pulse oximetry device 10. Each SpO2 measurement will be associated to an absolute or relative time at which it was taken. Note that, in simpler terms, it is possible to refer to this phase as the 'measurement' of SpO2 although, as previously explained, this is rather a calculation or estimation, or in yet other words an indirect measurement;
5) Memorise the measured SpO2 values in memory 18;
6) Download the measured SpO2 values to the docking station 30 or other device, as specified;
7) Manage the initial configuration of the pulse oximetry device 10;
8) Manage any additional function buttons (not shown) that may be provided with the device 10; and,
9) Manage the energy available in the battery, including providing for any power saving modes.

The PCB 17 was sourced from Microchip Technology Inc. with embedded microprocessor 19 and storage memory 18. However, other makes and/or architecture are possible although are not described here in detail.

The microprocessor 19 has 16-bit vertical resolution, 128 KB of serial FLASH memory and 16 KB of RAM memory embedded.

The storage memory 18 is a serial FLASH memory of 8 MB.

Other microprocessor capabilities and/or memory sizes could however be appropriate, depending on the application and/or performance requested.

The Bluetooth capability of the communication module (not shown) of the PCB 17 allows the device 10 to communicate with the docking station 30 as well as other Bluetooth enabled devices. An app may be envisaged to manage said data exchange processes.

SpO2 measurements obtained from a non-calibrated pulse oximetry device 10 of the type shown in FIGS. 1-3 have been shown to be only loosely in line with those obtained by a traditional, certified medical pulse-oximeter 100 such as that shown in FIG. 4. This can be addressed with the calibration procedure that will now be described.

Figure 9:
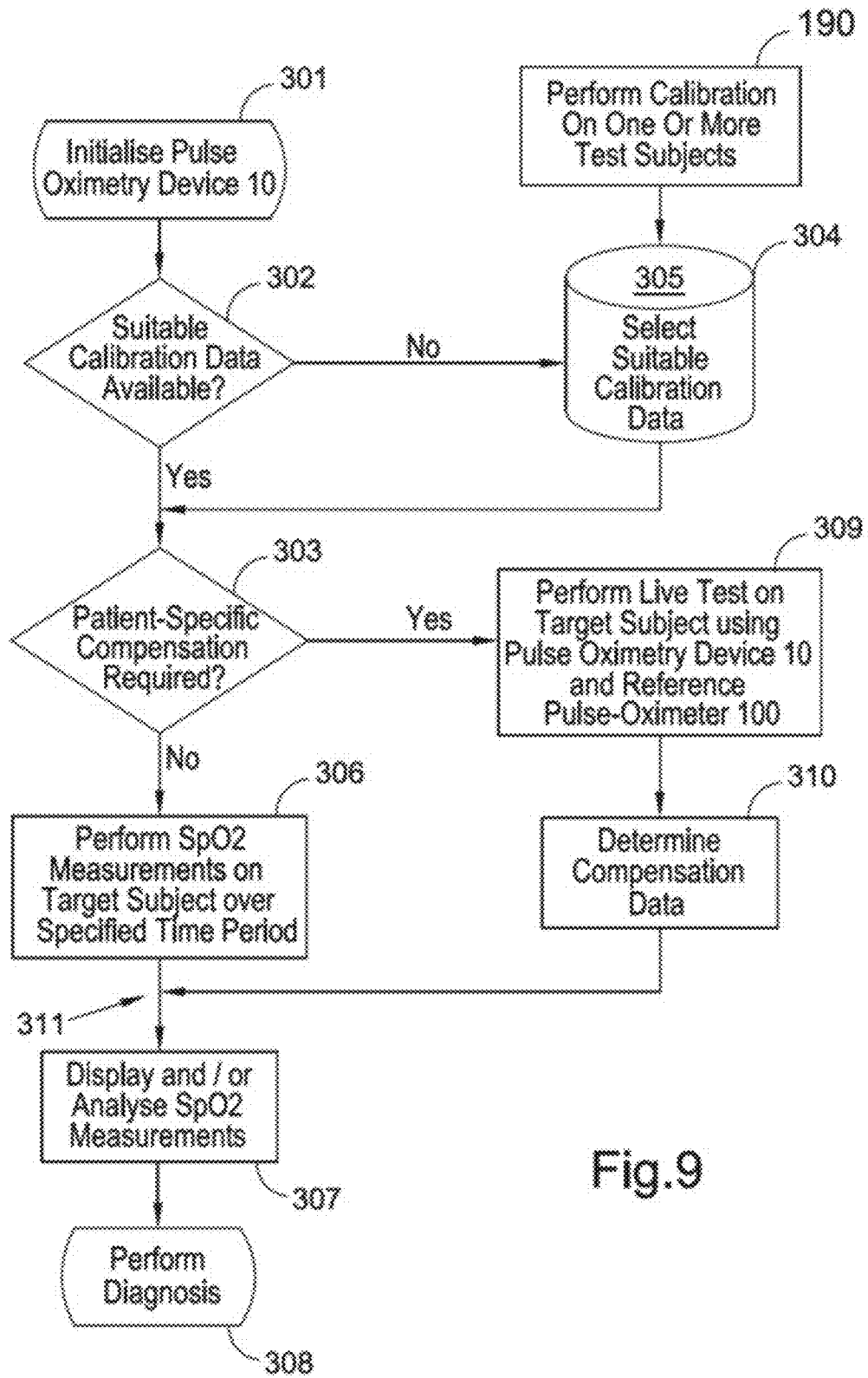
FIG. 9 is a flow chart illustrating steps of performing acquisition and monitoring of SpO2 measurements as described herein, and follow-on diagnosis.

FIG. 4 illustrates the general principle of the proposed calibration method 190 (also represented in FIG. 9). The wearable pulse oximetry device 10 of FIGS. 1-3 is calibrated against a medically graded pulse-oximeter 100 of conventional construction. The inventors have appreciated that by adopting this calibration procedure 190 the wearable pulse oximetry device 10 can measure SpO2 data of at least comparable quality with respect to those produced by the medical-grade pulse-oximeter 100. However, the advantage of the present bracelet-type pulse oximetry device 10, which includes a pulse oximeter in the form of a bracelet 10A, that is a bracelet-type pulse oximeter 10A, is that it is better suited than any traditional medical-grade pulse-oximeter 100 to monitor non-invasively and non-obstructively SpO2 during extended time windows, for example of the duration of many hours or days.

The calibration procedure 190 described herein was conducted on a test group of four subjects. However, it will be observed that the calibration procedure 190 is not so limited and fewer or more test subjects could have been chosen. Further, as it will be apparent from FIG. 9 described in more detail below, the calibration process 190 can in principle be carried out or repeated at any time and/or in preparation for any specific applications with an increased number of test subjects, or with different test subjects. Increasing the number of test subjects, or changing the test subjects, is believed to improve the quality of the final SpO2 measurements, for reasons that will be apparent from the description below.

During the tests carried out on the four patients, an SpO2 measurement frequency of one measurement every 10 seconds has been adopted. However, it will be appreciated that this is just an example and different measurement frequencies could have been used. The acquired data were memorized in the pulse oximetry bracelet 10 to represent a time period of up to 24 hours. The data were then transferred from the pulse oximetry device 10 to the docking station 30. This is just an example, since the data could have equally been transferred to a PC, or from the docking station 30 to a PC, prior to processing and display and/or analysis.

For each subject, the device 10 was positioned on the left wrist in the position shown in FIG. 4. To make sure that the device 10 could pick up an appropriate PPG signal we checked that the peak amplitude of the infrared signal was at least 100 units through the software interface MAX30102 EV kit provided by Maxim Integrated, Inc. together with the pulse oximetry unit 9. The location of the sensor can be adjusted on the backface or underside of the wrist until a reasonable, optimum or maximum signal is detected.

In order to obtain reference measurements of SpO2, each subject also wore on the left index finger a Nonin medical grade pulse oximetry device model 2500A, used herein as the reference pulse-oximeter 100. Measurements of SpO2 (and heart rate) were thus available from this medical grade reference device 100 as well as from the device 10 to be calibrated. It is observed that while the medical grade reference device 100 performed measurements in 'light transmission' mode, the pulse oximetry device 10 undergoing calibration operated in 'light reflection' mode. Whilst this is the case in the described calibration procedure 190, alternative calibration procedures may encompass alternative devices 10, 100 and different combinations of operations modes, including 'mixed' operations modes (ie wherein the light detected may have been partly transmitted and partly reflected before it is detected in the form of the PPG signal).

Further, in the described calibration procedure 190, the devices 10, 100 inferred SpO2 on the basis of the same parameter R evaluated from the detected light. The formulation of R is provided below. However, it will be appreciated that the proposed calibration procedure 190 is in principle independent from the actual parameters evaluated by the specific devices 10, 100 used in the process 190. The concept underlying the present disclosure is that of calibrating a wearable pulse oximetry device 10, such as the bracelet-type pulse oximetry device 10 described herein, that is adapted to measure SpO2 in zones of relatively low blood perfusion, against measurements taken by a pulse-oximeter 100 such as the Nonin device used herein, on zones of relatively higher blood perfusion, independently from how each instrument actually evaluates SpO2.

Returning to the tests, subjects 1, 3 and 4 were asked to remain seated, breathe initially in a normal way, keep a left arm at rest (motionless, but sufficiently firm) and follow the protocol described below:

a. 2-3 minutes of normal breathing;
b. Apnea for as long as possible;
c. 3-4 minutes of recovery time with normal breathing;
d. Apnea for as long as possible;
e. 2-3 minutes of recovery time with normal breathing.

Subject 2, who was an asthma sufferer, was asked to breathe normally while a mask administered a gaseous mixture with oxygen up to 60%.

For each test subject, the following experimental data were acquired by the light detector 13 of device 10:
the intensity of the reflected infrared light as a function of time (ie infrared waveform); and,
the intensity of reflected red light as a function of time (ie red waveform).

The above signals each represent a PPG signal in the described set-up. In alternative set-ups, at least in principle, only one signal could be used insofar as the underlying light is sufficiently affected by absorption in connection with oxygen transported by hemoglobin as it travels the target blood-perfused tissue.

Further, the acceleration of the pulse oximetry device 10 as measured by the triaxial accelerometer 36 according to each of three reference axes Ay, Ax and Az was also recorded.

Using the reference pulse-oximeter 100, SpO2 was also recorded as a function of time in correspondence with the measurements taken by the pulse oximetry device 10, which was the device being calibrated.

All the data acquired from the pulse oximetry device 10 were eventually stored on a PC, and the corresponding waveforms processed to provide input to a mathematical algorithm (know in the art) to calculate the SpO2, thus simulating on the PC the processing and calculation of parameters which in real life would be done by the onboard microcontroller 19 of the device pulse oximetry 10.

The measurements of SpO2 achieved by the reference pulse-oximeter 100 were plotted against the corresponding values of the parameter R achieved by the pulse oximetry device 10 undergoing calibration.

R is mathematically calculated from the amplitude of the continuous (DC) and alternating (AC) red and infrared components of the reflected light signals acquired by the pulse oximetry device 10 as follows:

$$R = \frac{RedAC/RedDC}{InfraRedAC/InfraRedDC}.$$ Equation 1

Figure 8:
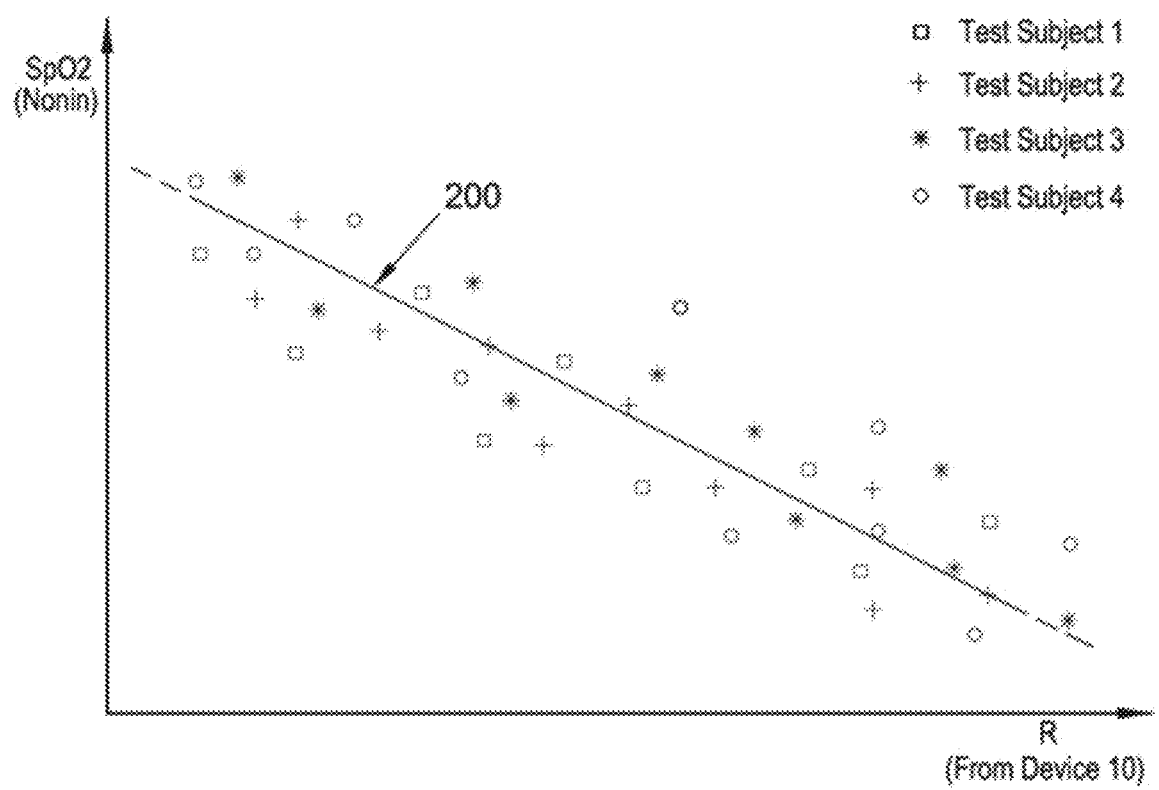
FIG. 8 is a graph illustrating the derivation of a calibration curve/function for the pulse oximetry devices of FIGS. 1-6.

A merely illustrative graph is shown in FIG. 8, for each of the four tested patients.

In the described calibration procedure 190 illustrated (purely schematically) by FIG. 8, the calibration curve 200 was obtained by linear interpolation of the plotted data pairs. In the calibration scenario 190 described herein, this corresponded to Equation 2 given below:

$$SpO2 = -39.4R + 112.9.$$ Equation 2:

Once calibrated according to the above Equation 2, the measurement of SpO2 on the pulse oximetry device 10 are performed accordingly. Equation 2 therefore expresses a single linear relation between SpO2 and the measured parameter R which was obtained experimentally as a calibration relationship for the device 10 on the basis of the four test subjects and the reference pulse-oximeter 100.

The quality of the heart rate measurement using the pulse oximetry device 10 was assessed by measuring an error as the standard deviation percentage calculated between the values obtained from the infrared and red waveforms acquired with the pulse oximetry device 10 and corresponding records performed on the same subject with the reference medical pulse-oximeter 100. The results were considered to be within acceptable error boundaries.

In order to recognize any events of hypoxia and to classify them correctly on the basis of their severity, the SpO2 data obtained from the calibrated device 10 were subsequently input to a classification algorithm that was built in accordance with the rules described hereinbelow.

Starting from values which expressed SpO2 as a percentage, the following colour groups were used to evaluate the severity of the events:

Green or class 1: SpO2>93%;
Yellow or class 2: SpO2 between 88% and 93%;
Orange or class 3: SpO2 between 83% and 88%;
Red or class 4: SpO2<83%.

An exemplary summary table is provided below:

TABLE 1

| | Total recorded time | Rest conditions, during the day | Rest conditions, at night | Presence of physical activity |
|---|---|---|---|---|
| Green SpO2 ≥ 93% | XX % HH:MM:SS | XX % HH:MM:SS | XX % HH:MM:SS | XX % HH:MM:SS |
| Yellow 88% ≤ SpO2 < 93% | XX % HH:MM:SS | XX % HH:MM:SS | XX % HH:MM:SS | XX % HH:MM:SS |
| Orange 83% ≤ SpO2 < 88% | XX % HH:MM:SS | XX % HH:MM:SS | XX % HH:MM:SS | XX % HH:MM:SS |
| Red SpO2 ≤ 83% | XX % HH:MM:SS | XX % HH:MM:SS | XX % HH:MM:SS | XX % HH:MM:SS |
| Total time | HH:MM:SS (100%) | HH:MM:SS (XX %) | HH:MM:SS (XX %) | HH:MM:SS (XX %) |

According to table 1, the SpO2 measurements were categorised according to their classes and according to three basic conditions that describe in broad terms the level of activity of the patients (rest during the day, rest at night and physical exercise), as inferred from the acceleration measurements obtained from the accelerometer 36. The duration of these events is provided in each window. Each window corresponds to one of the above classes and one basic patient condition.

The categorisation of the SpO2 measurements showed a satisfactory degree of consistency between the calibrated pulse oximetry device 10 and the reference pulse-oximeter 100.

Optimization Method

An optimisation method 309, 310, 311 is now described. This method is also labelled in FIG. 9 which is described further below. The optimisation method can further enhance the SpO2 measurements obtained from a calibrated pulse oximetry device 10.

The accuracy of the SpO2 measurements recorded using the bracelet-type pulse oximetry device 10A can be optimised, for each patient, by calculating an average of the SpO2 values measured by the reference pulse-oximeter 100 and by utilising this average to compensate a corresponding averaged value of SpO2 measured by the pulse oximetry device 10.

Offset Calibration

The inventors have recognised that this patient-specific optimisation procedure 309, 310, 311 can be beneficial to the quality of the measurements prior to recording SpO2 levels over extended time periods using the pulse oximetry device 10. We refer interchangeably in the present description to 'optimisation', 'correction' and/or 'compensation' of existing calibration data, where the existing calibration data could be the calibration data obtained according to the calibration procedure 190 described herein or calibration data obtained according to the prior art, that is in accordance with the 'golden standard' provided by in-vitro measurements of SaO2 in blood samples (this is a physical analysis of the oxygen as a gas dissolved in the blood as a liquid performed in the laboratory).

In other words, the 'dynamic' response of the device 10 (represented in the examples described herein by a line having an inclination, ie a non-zero angular coefficient) is inferred from the calibration procedure across many patients and a variety of potential conditions (alternatively, the 'golden standard' calibration curves could be used). The 'baseline' (ie, the offset of the line referred to above) is instead recognised to be patient-specific. As a consequence, the inventors have also appreciated that this baseline or offset could conveniently be determined for each patient by following this method:

providing a calibration pulse-oximeter (such as, but not limited to, the Nonin device described herein) adapted to estimate one or more first, reference SpO2 values from a first, reference PPG signal measured by the calibration pulse-oximeter on a first, reference area of the human body, such as a fingertip or an ear lobe, ie areas well perfused with capillary blood and that, as such, are likely to provide better SpO2 estimates than areas with lower levels of blood perfusion;

using the same or a different calibration pulse-oximeter, estimating one or more second SpO2 values from a second PPG signal measured by said same or different calibration pulse-oximeter on a second, target area of the human body, such as on the wrist, as described herein, and more particularly on the wrist underside; and, calculating a calibration parameter (that is a single calibration value) or calibration function on the basis of the one or more first, reference SpO2 values and the second SpO2 values. This calibration parameter or calibration function can then be used in future to correct any SpO2 measurements taken by any pulse-oximeter on the target area, providing as a result improved, ie more accurate, final SpO2 measurements.

Advantageously, the same pulse-oximeter could be used to perform the first and second SpO2 estimates on the different areas of the human body at different times, ie immediately first or immediately after one of the two sets of measurements has been taken first. Clearly, it is undesired to wait too long before taking the other set of measurements. This is to minimise any changes in the level of SpO2 dictated by potentially changing conditions of the test subject/patient. Taking the two sets of measurements within about an hour from each other could be satisfactory, but better would be to take the two sets of measurements temporally apart less than about half-hour, less than 10 minutes, less than 5 minutes, and, if possible, even less than a minute. The same pulse oximeter, for example the device 10 described herein, could in principle be used to perform the one or more SpO2 estimates on the first, blood-perfused region (eg, the fingertip); subsequently, it could be used to perform the SpO2 estimates on the second, less perfused region (eg, the wrist, and preferably the wrist underside) and it could then finally be used to perform regular, calibrated SpO2 measurements across an extended time period for example of about a day as described herein.

In its most basic implementation of offset calibration routine described herein, a single first estimate of SpO2 is taken on the finger tip of the test subject/patient using the sensor mounted on the device 10 described herein; then, after a few seconds (the time strictly required to make preparations for taking the second estimate), a single second SpO2 estimate is taken on the wrist, eg on the wrist underside (eg. at a specified predetermined location thereon which maximises signal-to-noise ratio for the device 10); then, an offset is calculated as the difference between the two estimates. This offset represents a type of calibration which is specific to the patient, and is therefore independent from any calibration curves derived from performing repeated tests on any given patients under different oxygenation conditions, and across many test subjects/patients. Accordingly, this offset can be independently used to improve SpO2 estimates for specific patients in conjunction with calibration curves obtained as described herein or in any other way, for example as described in the prior art.

To validate the proposed calibration compensation procedure 309, 310, 311, the data produced by the pulse oximetry device 10 were all compensated and then compared with the results obtained with the reference device 100. The results were satisfactory.

In the calibration procedure 190 described herein, SpO2 was estimated for each measurement on the basis of a linear regression calibration curve 200 that relates the SpO2 estimated using the reference device 100 and the parameter R calculated from the recorded signals with the pulse oximetry device 10. In the described calibration procedure 190, the experimental relationship between R and SpO2 was linear and defined by the below:

$$SpO2 = MR + Q, \quad \text{Equation 3}$$

where M and Q are coefficients obtained experimentally on the basis of the calibration measurements performed on multiple subject (these are schematically plotted in FIG. 8).

The inventors have realized that the above coefficients vary slightly from subject to subject. Equation 2 was derived to express a generalized or universal relation that links R and SpO2 for the device 10. This generalized relationship was taken as a calibration curve applicable to any target subjects on which SpO2 measurements are to be taken.

To optimize the estimation of SpO2 on the target subjects, the initial value of SpO2 measured with the reference pulse-oximeter 100 was saved and subsequently used to offset the measurements obtained with the pulse oximetry device 10. In this way, the measurement of SpO2 performed by the reference pulse-oximeter 100 on the finger served to determine a value of a patient-specific correction which would improve the accuracy of the final measurements by compensating for patient-specific characteristics such as, for example, the different characteristics of the skin between one subject and another.

On the phalanx or fore-finger it is possible to measure PPG signals of greater intensity and hence it is possible to estimate SpO2 with an accuracy greater than on the wrist, where, instead, in the case of the present pulse oximetry device 10 the IR and RED PPG signals are weaker and thus more affected by noise and artefacts.

In order to validate the optimization technique 309, 310, 311 described above using further sets of experimental acquisitions, it is proposed to carry out the following work plan:
1. Repeat the calibration procedure 190 on a larger group of test subjects with different characteristics (sex, age, skin, pigmentation, etc.);
2. Derive a new general or universal relation 200 according to Equation 2 and use the M and Q parameters so derived to evaluate a predicted error on each of the SpO2 records concerned;
3. Compensate the measured SpO2 values with the optimization procedure described herein and evaluate an error on the SpO2 measurements after compensation; and
4. Compare the two techniques (with or without compensation) for measuring SpO2 to determine and quantify any improvement obtained.

In a practical clinical application, a correction value in accordance with the optimization method described herein can be obtained by asking the patient to wear a first pulse oximetry device 10 as described herein, waiting 2-3 minutes for the adaptation of the skin to the pressure exerted by the device 10, then performing measurements of SpO2 with the device 10 and with a second, reference pulse-oximeter 100 applied on the index finger of one hand. This second, reference pulse-oximeter 100 can preferably be integrated into the docking station 30.

To validate the proposed technique, the experimental data captured during the tests described above have been used to simulate any improvements which could be obtained by applying the present optimisation method, according to the following routine:
1. We considered the acquisition time windows for all test subjects from the $60^{th}$ second to the $150^{th}$ second;
2. For each time window, and for each test subject, we averaged the SpO2 measurements obtained with the reference medical device 100 (|SpO2Ref|);
3. For each time window, and for each patient, we averaged the SpO2 measurements obtained from the calibrated pulse oximetry device 10 (|SpO2Dev|);

4. We then calculated an offset between the two measurements as:

$$\text{offset}=|\text{SpO2Dev}|-|\text{SpO2Ref}|; \quad \text{Equation 4:}$$

5. The SpO2 measured from the calibrated pulse oximetry device 10 was optimised according to the equation:

$$\text{SpO2Opt}=\text{SpO2Dev}-\text{offset}, \quad \text{Equation 5:}$$

wherein SpO2Opt is the optimized measurement.

After the above offset was applied to the SpO2 values measured with the device 10, the results were used again in the classification algorithm described above in relation to Table 1, with substantial quality improvements of the clinical assessment.

FIG. 9 is a flow chart that illustrates a procedure for achieving diagnosis based on the measurements of medical grade SpO2 values using a calibrated pulse oximetry device 10 as described herein. Accordingly, FIG. 9 provides the context of the calibration procedure 190 and for the optimization procedure 309, 310, 311 described above.

The pulse oximetry device 10 initially undergoes initialisation 301, which may comprise operations known in the art such as checking that the battery of the device 10 is sufficiently charged and that the memory 18 is sufficiently free to store the required data.

The operator then decides 302 whether any existing calibration data are appropriate for the intended clinical application.

If the pulse oximetry device 10 is adequately calibrated, then in the next step 303 the operator decides whether any patient-specific compensation of the to-be-acquired SpO2 measurements is required. This is for example the case when the pulse oximetry device 10 uses a generalized or universal calibration curve 200 of the type discussed herein. However, it may be the case that patient-specific compensation is not required. This happens when the pulse oximetry device 10 is already programmed with a patient-specific calibration curve. For test subjects 1 to 4 referred to in FIG. 8, such a calibration curve would be expressed for each subject according to Equation 3, on the basis of the respective calibration tests, with the coefficients M and Q being thus patient-specific.

If patient-specific compensation is not required, then the pulse oximetry device 10 can be provided to the target subject who wears it for an agreed time period while the pulse oximetry unit performs the required measurements. The pulse oximetry device 10 first measures the parameter R and, then, converts these R values into corresponding values of SpO2 on the basis of the calibration data loaded on the pulse oximetry device 10. This is exemplified by block 306 in FIG. 9.

The data acquired are then displayed on a display 50, for example such as the one shown in FIG. 7 and/or they are then analysed. This step is represented in FIG. 9 by block 307.

If the pulse oximetry device 10 is not adequately calibrated for the proposed clinical application, then the operator has a choice of consulting a database 305 to select an appropriate calibration curve. This is represented in FIG. 9 by step 304.

The calibration curves are divided in the database 305 into calibration libraries each referring to one or more test subjects categorised according to certain characteristics such as sex, age group, race, etc. The calibration libraries can include new calibration curves obtained with the calibration procedure 190 described herein and from time to time uploaded to the database 305.

Another way of classifying the calibration curves is, for example, based on the type of pulse oximetry sensing unit 9 and/or pulse oximetry device 10 used to take the measurements, and/or on the basis of the reference pulse-oximeter 100 used to obtain the calibration curves. In this way, the operator ensures that the selected calibration curve is for the correct pulse oximetry device 100 and refers to a desired reference pulse-oximeter 100. In the lack of information on the clinical application, a generalised calibration relation can be used of the kind expressed by Equation 2 above.

If a generalised calibration relationship is used, then the operator may decide 303 that patient specific compensation is advisable and/or required. A 'live' test can then be performed (step 309) on the target subject using the pulse oximetry device 10 and an appropriate reference oximeter 100, as described above. The SpO2 measurements obtained in this live test can then be used to derive one or more compensation parameters (step 310), also as described above. Finally, the compensation parameters can be used to alter the SpO2 measurements after that these have been taken (junction/step 311).

The resulting diagnosis 308 is provided on data sets which are more accurate and/or more consistent with respect to the prior art. Further, these SpO2 data are taken using the pulse oximetry device 10 over large time periods while the target patient carries out normal daily activities. This further enhances the probability to achieve correct diagnosis.

Provision of Multiple Pulse Oximetry Sensing Units on the Device

The inventors have also appreciated that it may be desirable to provide a plurality of (that is two or more) pulse oximetry sensing units 9A, 9B, 9C on the same device 10, and an example is illustrated in FIG. 10. The pulse oximetry sensing units 9A, 9B, 9C are arranged in a spatially distanced configuration on the bottom face 5 of the case 11 of the bracelet-type pulse oximeter 10A.

Each sensing unit 9A, 9B, 9C in FIG. 10 is exactly as described above, that is each comprises red and infrared emitters 2, 3 and a photodetector 13. It is important to reaffirm that said colours could be different, for example one could be green. Further, it is not necessary that the light emitters be just two in each pulse oximeter sensing unit 9A, 9B, 9C, as thee could be just one or more than two, for example three. When three light emitters are present in each sensing unit, the corresponding lights could be red, green and infrared.

From each light emitter 2, 3 of each sensing unit 9A, 9B, 9C light is shone on the wrist underside, and light reflected back or scattered back to each photodetector 13 of each sensing unit 9A, 9B, 9C is detected and converted into a corresponding PPG signal 1 (examples of which are purely illustratively shown in FIG. 7).

Each sensing unit 9A, 9B, 9C thus measures at least one PPG signal 1 (and as many as the light emitters 2, 3) during a measurement interval (whose duration can be set arbitrarily, as discussed above), and the device 10 converts said measured PPG signals 1 (red and infrared in the presently described example) into a respective SpO2 measurement.

Each pulse oximetry sensing unit 9A, 9B, 9C has previously been calibrated according to the calibration procedure 190 described hereinabove. If universal calibration curves are used (for example, derived according to the 'golden standard' of SaO2) then each pulse oximetry sensing unit 9A, 9B, 9C has been at least corrected/optimised by the application of the 'offset' procedure as described herein.

Either way, each pulse oximetry sensing unit 9A, 9B, 9C has been calibrated according to a respective, sensing unit-specific calibration parameter or calibration function obtained as described herein, and that is:

using a calibration pulse-oximeter 100, estimating one or more first, reference SpO2 values from a first, reference PPG signal measured by the calibration pulse-oximeter on a first, reference area of the human body;

using the bracelet-type pulse oximeter 10A, estimating one or more second SpO2 values from a second PPG signal 1 measured by a respective pulse oximetry sensing unit 9A, 9B, 9C on the wrist underside, wherein the first, reference area of the human body has greater blood perfusion than the wrist underside;

calculating the respective, sensing unit-specific calibration parameter or calibration function on the basis of the one or more first, reference SpO2 values and the one or more second SpO2 values.

It will be appreciated that the calibration and offset adjustment processes described herein are not mutually exclusive. That is, for each sensing unit 9A, 9B, 9C first the calibration procedure 190 could be carried out, then the patient-specific offset adjustment could be applied. It is possible, however, that useable calibration curves may already be available, whereby the patient-specific offset adjustment is the only required step prior to commencing data acquisitions on a user or patient. When suitable calibration curves already exist, for each sensing unit 9A, 9B, 9C it may be easier to perform the offset calculation routine using the bracelet-type pulse oximeter 10A, on a sensing unit by sensing unit basis, one at a time, by measuring SpO2 values on, for example, the fingertip and wrist underside.

The device 10 is herein adapted to calculate for each sensing unit at least one sensing unit-specific mathematical parameter R as follows:

$$R = \frac{RedAC/RedDC}{InfraRedAC/InfraRedDC},$$

wherein, RedAC is an AC component of the light having the red wavelength; RedDC is a DC component of the light having the red wavelength; InfraRedAC is an AC component of the light having the infrared wavelength; and InfraRedDC is a DC component of the light having the infrared wavelength.

The device 10 is adapted to convert for each sensing unit 9A, 9B, 9C the measured PPG signals 1 into the respective SpO2 measurement as a function of said parameter R. In other words, the device/pulse oximeter 10 converts R into SpO2 for each pulse oximetry sensing unit 9A, 9B, 9C.

The advantage of having spatially distributed sensing units 9A, 9B, 9C is that during any one measurement interval, the measured SpO2 can more reliably be calculated based upon any subgroup of the sensing units 9A, 9B, 9C. In other words, during any one measurement interval, it is assumed that at least one of the sensing units 9A, 9B, 9C will provide the PPG acquisitions necessary for the calculation of the SpO2 (or, if this condition is not verified, then for that measurement interval no reliable SpO2 measurement is recorded). However, there could be at least two or more sensing units 9A, 9B, 9C with acquired PPG signals 1 which are of quality sufficient to be relied upon for the calculation of the SpO2.

The inventors have understood that the quality of the PPG signals measured on the wrist increases with the proximity of the sensing units 9A, 9B and 9C to the ulnar artery 400 on the wrist underside (this is visible in FIG. 11). Depending on patient-specific morphologies, other arteries at the wrist may be suitable, for example the radial artery. However, the radial artery is generally less advantageously positioned for pulse oximetry measurements on the wrist underside. It will also be appreciated that while in the present description we generally refer to the "wrist underside" for clarity and simplicity, anatomically it would be likewise appropriate to refer to the "distal underside of the forearm" as the target area for the SpO2 measurements.

In the device 10 shown in FIGS. 10 and 11, the processor 19 is programmed to associate to each measured PPG signal 1 at least one score representative of measurement quality during the measurement interval. The processor 19 is also programmed to carry out the conversion of the measured PPG signals 1 considering said scores. For example, the processor 10 could decide which sensing unit 9A, 9B, 9C has the best combined score for the respective Red and Infrared PPG signals, and base the SpO2 measurement in the measurement interval in question upon the selected sensing unit 9A, 9B, 9C. Similarly, any one or more sensing units that have measured PPG signals 1 of dubious quality may be excluded from the conversion into SpO2. Likewise, there may be two or more sensing units that have measured PPG signals 1 of good enough quality to participate in the SpO2 measurement. This can be done for example on the basis of a weighted average across the chosen one or more sensing units 9A, 9B, 9C, where the weights used in the weighted average may be a calculated on the basis of the quality scores of (for example the weights could be proportional to) the PPG signals 1.

Returning to the determination of the quality scores, the bracelet-type pulse oximeter 10 comprises the accelerometer 36 and therefore at least one of said scores can be determined as being inversely related to a first correlation factor between a signal output by the accelerometer 36 during the measurement interval, and the PPG signal 1 measured during the measurement interval. The more the PPG signal is correlated to the acceleration signal, the more the PPG signal is likely to suffer from the presence of an artefact.

Another manner of determining the quality scores is to determine a second correlation factor between the PPG signal measured during the measurement interval and a comparison signal (a benchmark) obtained as an average of other PPG signals measured by the device 10, which could for example be all other measured PPG signals, or a subset thereof.

Another manner of determining the quality scores is to perform a time domain analysis of the PPG signal. For example, one could determine a score based upon the repeatability of peak-to-peak amplitudes of the PPG signal 1 during the measurement interval: the more repeatable are such amplitudes, the more reliable the PPG signal is and the higher the quality score. Alternatively, one could determine the score based upon the absolute values of the peak-to-peak amplitudes of the PPG signals 1 and/or an absolute value of the mean amplitudes of the PPG signals 1 during the measurement interval.

Another manner of determining the quality scores is to perform a frequency domain analysis of the PPG signal. For example, one could determine the scores based upon an analysis of a spectrum, such as a power spectrum, of the PPG signal 1. For example, the scores could be based upon parameters such as spectral skewness and/or a spectral standard deviation around a main frequency of said spectrum of the PPG signal, with the better scores assigned to symmetric spectra.

Accordingly, the provision of multiple pulse oximetry sensing units onboard a single bracelet-type device 10, 10A enables a large variety of strategies for the selection of one or more sensing units deemed at any one measurement time sufficiently reliable to be relied upon to provide the sought SpO2 measurement. At the basis of these strategies, however, there is the capability of attributing quality scores to the underlying PPG signals. Some sensing units might be excluded from said measurement because, at the time of measurement, one or more respective PPG signal was of insufficient quality. When more than a single sensing unit can be relied upon, then the measured SpO2 will be a weighted average of measured, sensing-unit specific SpO2 values, wherein the weights of the weighted average are determined based upon the quality scores of the PPG signals 1.

An alternative but still viable strategy for the measurement of the SpO2 could be to exclude any pulse oximetry sensing units 9A, 9B, 9C and then average the PPG signals by colour before the R calculations are performed.

Another important variable in the provision of multiple sensing units 9A, 9B, 9C is the spatial configuration of the sensing units 9A, 9B, 9C, which in FIG. 10, by way of example only, are shown in a generally triangular configuration. It is possible to increase the number of sensing units in the device 10, 10A. However, there are space limits imposed by the case 11, which should be of an acceptable size. Nevertheless, it is possible to have more than just three sensing units, for example four, five or six sensing units.

The sensing units can be disposed in the shape of a polygon, for example a regular polygon. Alternative configurations are however possible, such as in linear configuration, in T-shaped, L-Shaped, Y-shaped, star-shaped or cross-shaped configurations.

The plurality of sensing units is deemed advantageous since, depending on the morphology of the user or patient in question, as the number of sensing units increases the likelihood of placing at least one sensing unit in proximity of an artery, such as the ulnar artery 400, increases. Although such at least one sensor may not be the only sensor that acquires PPG signals of good quality, and therefore the only sensor on which measurement of SpO2 can be based, it is important to ensure that at any one time there are good probabilities that at least one sensor is located at a reliable measurement location on the wrist underside.

The three pulse oximetry sensing units 9A, 9B, 9C shown in FIG. 10 enable better probabilities of having at least one sensing unit in a good measurement location on the wrist underside as compared to having a single sensor 9 (as shown in FIG. 2), or two sensors (this configuration is not shown in the Figures) disposed on the back face 5 of the case 11 of the bracelet-type pulse oximeter 10A.

LIST OF REFERENCES

1 PPG signal; 2, 3, 2', 3' light emitters; 5, 5' back face of device; 6 front face of case; 8, 8' window; 9, 9' pulse oximetry sensing unit; 9A, 9B, 9C pulse oximetry sensing units; 10, 10' pulse oximetry device; 10A bracelet-type pulse oximeter or bracelet; 11, 11' case; 12, 12' strap; 13, 13' light detector; 14, 14' bottom case part; 15 top case part; 16 alarm light; 17 PCB; 18 memory; 19 processor; 20 inner side of top case part; 21 recharge coil; 22 inner side of bottom case part; 23 first recess; 24 second recess; 25, 25' projection; 26, 27 matching profiles; 28, 28' screws; 29 bore holes; 30 docking station; 36 accelerometer; 40 rubber insert; 50 display; 100 reference pulse oximeter; 190 calibration method; 200 calibration curve or function; 301 initialising the procedure; 302 deciding on availability of suitable calibration curves; 303 deciding whether patient-specific compensation is required; 304 consulting database of calibration curves; 305 database; 306 converting into SpO2 values; 307 displaying data; 308 performing diagnosis; 309 performing one or more live tests on a test subject using the measurement pulse oximetry device and the reference pulse oximeter (to determine a patient-specific offset parameter); 310 determining the offset parameter; 311 applying the offset parameter; and 400 ulnar artery.

The invention claimed is:

1. A method of taking pulse oximetry measurements on a specific patient, the method comprising:
    using a calibration pulse-oximeter, estimating one or more first, reference SpO2 values from a first, reference PPG signal measured by the calibration pulse-oximeter on a first, reference area of the human body of said specific patient;
    wherein said calibration pulse-oximeter comprises one or more light emitters adapted to emit light directed into a human tissue, and at least one light detector for detecting light reflected from said tissue;
    wherein the first, reference area of the human body of said specific patient is a fingertip or an ear lobe of said specific patient, having greater blood perfusion than a second, target area of the human body of said specific patient located generally on an underside of a wrist of said specific patient;
    using the calibration pulse-oximeter, estimating one or more second SpO2 values from a second PPG signal measured on said second, target area of the specific patient;
    calculating an offset parameter on the basis of the one or more first, reference SpO2 values and the one or more second SpO2 values; and
    using a bracelet-type measurement pulse-oximetry device also comprising one or more light emitters adapted to emit light directed into a human tissue, and at least one light detector for detecting light reflected from said tissue, measuring a third PPG signal from the second, target area of the specific patient and estimating one or more third SpO2 values from the third PPG signal, wherein said third SpO2 values are offset using said offset parameter.

2. The method according to claim 1, wherein the second one or more SpO2 values are estimated immediately before or immediately after the first, reference one or more SpO2 values have been estimated.

3. The method according to claim 1, wherein the bracelet-type measurement pulse oximetry device is also used as the calibration pulse-oximeter.

4. A method according to claim 3, wherein the bracelet-type measurement pulse oximetry device comprises a case and a strap, wherein the case accommodates a pulse oximetry unit comprising:
    said two light emitters, wherein said two light emitters are each adapted to emit substantially monochromatic lights at different wavelengths comprising a red wavelength and an infrared wavelength; and
    said light detector;
    and wherein the strap comprises:
        a flexible elongated element connected to the case.

5. The method according to claim 4, further comprising applying the bracelet-type measurement pulse oximetry device to the wrist underside of said specific patient such that the light emitters are adapted to emit light into the underside of the wrist of said specific patient, and such that the light detector detects reflected light from the wrist underside of said specific patient.

6. The method of claim 5, wherein applying the bracelet-type pulse oximetry device to the wrist underside comprises identifying at least one position of the bracelet- type pulse oximetry device relative to the wrist underside which optimizes and/or maximizes a signal to noise ratio in relation to the third PPG signal.

7. The method according to claim 6, wherein applying the bracelet-type measurement pulse oximetry device to the wrist underside comprises marking the wrist with reference markers for positioning the pulse oximetry device relative to the wrist.

8. A method according to claim 6, wherein applying the bracelet-type measurement pulse oximetry device to the wrist underside comprises affixing one side of a double-sided adhesive element around a protrusion provided on a backside of the bracelet-type measurement pulse oximetry device, wherein said protrusion is arranged to cooperate with the two light emitters and with the light detector for emitting and detecting said light and to grip the wrist underside.

9. The method according to claim 8, wherein applying the bracelet-type measurement pulse oximetry device to the wrist underside comprises affixing the bracelet-type measurement pulse oximetry device to the wrist underside via the other side of the double-sided adhesive element.

10. The method according to claim 1, wherein the offset parameter is calculated from at least one of a single first, reference SpO2 value and a single second SpO2 value.

11. The method according to claim 1, wherein the calibration pulse-oximeter and the bracelet-type pulse oximetry device are each adapted to calculate a same mathematical parameter from the respective measured PPG signal.

12. The method according to claim 1, wherein the calibration pulse-oximeter used for estimating said first, reference one or more SpO2 values is a medical-grade pulse-oximeter.

13. The method according to claim 12, wherein the medical-grade pulse-oximeter is a medically certified pulse oximeter.

14. The method according to claim 1, wherein the light detectors are each adapted to measure a light intensity.

15. A method according to claim 14, wherein said light emitters are adapted to emit two respective substantially monochromatic lights at different wavelengths, wherein said different wavelengths comprise a red wavelength and an infrared wavelength.

16. A method according to claim 15, wherein the calibration pulse-oximeter and the bracelet-type measurement pulse oximetry device are each adapted to calculate a same mathematical parameter from the respective measured PPG signal, and wherein the mathematical parameter is a parameter R calculated as follows:

$$R = \frac{RedAC/RedDC}{InfraRedAC/InfraRedDC}$$

wherein,
RedAC is an AC component of the light having the red wavelength;
RedDC is a DC component of the light having the red wavelength;
InfraRedAC is an AC component of the light having the infrared wavelength; and,
InfraRedDC is a DC component of the light having the infrared wavelength.

17. The method according to claim 1, further comprising:
storing the offset parameter in a memory provided in the bracelet-type measurement pulse-oximetry device.

18. A bracelet-type pulse oximetry device for measuring blood oxygenation on a wrist underside of a specific patient, the bracelet-type pulse oximetry device comprising a bracelet and a case, wherein the case accommodates:
one or more light emitters adapted to emit light directed into said wrist underside and from there into a human tissue;
at least one light detector for detecting said light after the light has reflected from said human tissue;
a memory; and,
a processor,
wherein the processor and the memory are adapted to convert one or more measured characteristics of the detected light into corresponding SpO2 measurements according to the method of claim 3.

19. A system comprising, in combination, the bracelet-type measurement pulse oximetry device of claim 18 and a docking station for docking the device thereto, wherein the bracelet-type measurement pulse oximetry device and the docking station are operable to exchange data therebetween.

20. A system according to claim 19, wherein the docking station is adapted to wirelessly recharge the bracelet-type measurement pulse oximetry device.

* * * * *